US012718916B2

(12) United States Patent
Webster et al.

(10) Patent No.: US 12,718,916 B2
(45) Date of Patent: Aug. 25, 2026

(54) SITUATION REPORTING USING A WEARABLE MEDICAL DEVICE

(71) Applicant: West Affum Holdings Designated Activity Company, Dublin (IE)

(72) Inventors: Brian D. Webster, Mercer Island, WA (US); Jeffrey M. Boschee, Woodinville, WA (US)

(73) Assignee: West Affum Holdings DAC, Dublin (IE)

( * ) Notice: Subject to any disclaimer, the term of this patent is extended or adjusted under 35 U.S.C. 154(b) by 297 days.

(21) Appl. No.: 18/544,397

(22) Filed: Dec. 18, 2023

(65) Prior Publication Data

US 2024/0282421 A1 Aug. 22, 2024

Related U.S. Application Data

(60) Provisional application No. 63/446,486, filed on Feb. 17, 2023.

(51) Int. Cl.
*G16H 15/00* (2018.01)
*A61N 1/39* (2006.01)
(Continued)

(52) U.S. Cl.
CPC ........... *G16H 15/00* (2018.01); *A61N 1/3943* (2013.01); *A61N 1/3993* (2013.01); *G16H 40/67* (2018.01); *G16H 50/20* (2018.01)

(58) Field of Classification Search
CPC ........ G16H 15/00; G16H 40/67; G16H 50/20; G16H 10/60; G16H 40/20; G16H 20/30;
(Continued)

(56) References Cited

U.S. PATENT DOCUMENTS 3,724,355 A 4/1973 Busch et al.
3,724,455 A 4/1973 Unger
(Continued)

FOREIGN PATENT DOCUMENTS

DE 102005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Ryan W Sherwin
(74) *Attorney, Agent, or Firm* — Lisa Benado, Propel IP Law, PLLC

(57) ABSTRACT

The present medical support system produces situation reports about a patient experiencing a medical event. A wearable medical device worn by the patient when in use, gathers patient data from which situation reports are generated. The support system uses situation factors associated with the medical event to generate from the patient data, situation reports including situation information associated with the medical event. A rapid communication connection is established between the device of the support person and the wearable medical device and/or remote computing device(s), such as a BLE connection, QR code, etc. The support system presents the adapted situation reports from the remote computing device to various support persons assisting the patient during a critical time for care. In some implementations, the situation reports are generated on the fly according to levels of expertise of the support person.

20 Claims, 7 Drawing Sheets

(51) Int. Cl.
*G16H 40/67* (2018.01)
*G16H 50/20* (2018.01)

(58) Field of Classification Search
CPC .... G16H 40/63; A61N 1/3943; A61N 1/3993; A61N 1/046; A61N 1/39044; A61N 1/3904; A61N 1/3925
See application file for complete search history.

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Lapanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,659,484 B1 5/2017 Mehta et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,076,656 B2 9/2018 Dar et al.
10,192,387 B2 1/2019 Brinig et al.
10,307,133 B2 6/2019 Kaib
10,447,865 B2 10/2019 Mehta et al.
10,463,867 B2 11/2019 Kaib et al.
10,589,110 B2 3/2020 Oskin et al.
10,599,814 B2 3/2020 Landrum et al.
11,210,919 B2 12/2021 Beyer et al.
11,641,575 B2 5/2023 Horelik et al.
11,659,375 B2 5/2023 Anand et al.
11,741,819 B2 8/2023 Katz et al.
11,818,639 B2 11/2023 Horelik et al.
12,020,548 B2 6/2024 Jafri et al.
12,047,858 B2 7/2024 Anand
12,063,581 B2 8/2024 Martin et al.
2002/0181680 A1 12/2002 Linder et al.
2003/0004547 A1* 1/2003 Owen .................... A61N 1/046 607/5
2003/0158593 A1 8/2003 Heilman et al.
2003/0233129 A1* 12/2003 Matos .................. A61N 1/0476 607/5
2005/0107833 A1 5/2005 Freeman et al.
2005/0107834 A1 5/2005 Freeman et al.
2006/0173499 A1 8/2006 Hampton et al.
2008/0001735 A1* 1/2008 Tran ...................... A61B 5/1118 340/539.22
2008/0312709 A1 12/2008 Volpe et al.
2009/0005827 A1 1/2009 Weintraub et al.
2010/0007413 A1 1/2010 Herleikson et al.
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.

(56) References Cited

U.S. PATENT DOCUMENTS

2014/0070957 A1 3/2014 Longinotti-Buitoni et al.
2014/0154987 A1* 6/2014 Lee ........................ H04W 4/80 455/41.2
2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0304478 A1* 10/2015 Kim ...................... G16H 40/63 455/414.3
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.
2017/0027469 A1 2/2017 Amir et al.
2017/0036066 A1 2/2017 Chahine
2017/0040758 A1 2/2017 Amir et al.
2017/0162840 A1 6/2017 Pendry
2017/0281462 A1* 10/2017 Freeman .............. A61N 1/0484
2017/0319862 A1 11/2017 Foshee, Jr. et al.
2017/0367591 A1 12/2017 Jorgensen
2018/0040221 A1* 2/2018 Yao .................. H04M 1/72454
2018/0116537 A1 5/2018 Sullivan et al.
2018/0117299 A1 5/2018 Gustavson et al.
2018/0184933 A1 7/2018 Sullivan et al.
2018/0185662 A1 7/2018 Foshee, Jr. et al.
2018/0243578 A1 8/2018 Volosin
2018/0361165 A1 12/2018 Jaax et al.
2019/0030352 A1 1/2019 Sullivan et al.
2019/0076666 A1 3/2019 Medema
2019/0116896 A1 4/2019 Armour et al.
2019/0321650 A1 10/2019 Raymond et al.
2021/0228893 A1* 7/2021 Akram ................ A61N 1/3925
2023/0066525 A1 3/2023 Cabanas et al.
2023/0123348 A1 4/2023 Mehta et al.
2023/0336958 A1 10/2023 Mehta et al.
2023/0410635 A1 12/2023 Katz et al.
2024/0048952 A1 2/2024 Seidberg et al.
2024/0114328 A1 4/2024 Mehta et al.
2024/0144802 A1 5/2024 Beyer et al.
2024/0267719 A1 8/2024 Pellegrini et al.
2024/0276193 A1 8/2024 Martin et al.
2024/0292201 A1 8/2024 Katz et al.
2024/0334172 A1 10/2024 Bozik et al.

FOREIGN PATENT DOCUMENTS

JP 2005507747 A 3/2005
JP 2014500099 A 1/2014
JP 2014526282 A2 10/2014
WO 9839061 A1 9/1998
WO 2011/146448 A1 11/2011
WO 2012/064604 A1 5/2012
WO 2012/151160 A1 11/2012
WO 2015/056262 A1 4/2015
WO 2023107404 A2 6/2023

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi: 10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

500

SITUATION REPORTING USING A WEARABLE MEDICAL DEVICE

CROSS REFERENCES TO RELATED APPLICATIONS

This application claims the benefit of the filing date of U.S. Provisional Patent Application No. 63/446,486, filed Feb. 17, 2023, the disclosure of which is hereby incorporated herein by reference for all purposes.

FIELD OF THE INVENTION

The present disclosure generally relates to generating adapted reports for use in caring for patients.

BACKGROUND

Frequently medical emergencies require that a patient promptly receive treatment to attain a positive outcome. Some wearable medical devices can monitor a patient as the patient goes about day-to-day activities. Along the way, the wearable devices can accumulate a plethora of information about the patient. In some cases, the wearable medical devices can also deliver immediate treatment to the patient on the fly. Despite the health benefits of wearable medical devices, there is often additional need for human intervention to provide immediate care to the patient.

When a medical emergency happens while a patient is in the field away from a medical facility, the patient may be passed from support person to support person along a chain of care before arriving at a medical site. Each support person in the chain of care can gain from information about the patient's current and previous situation to use in providing various levels of care to the patient. Different supporting persons, such as bystanders, EMS persons, emergency room staff, etc. may need to quickly evaluate the situation of the patient before tending to the needs of the patient. For example, a description of treatment dispensed by the wearable medical device for the medical event can be important information for a support person.

A medical event that includes a heart arrhythmia for example, involves the heart ceasing to properly pump blood throughout the body. The malfunction can lead to collapse, unconsciousness, and death of the patient if not treated immediately. The longer the patient is in sudden cardiac arrest (SCA) or re-cardiac arrest, chances of survival goes down. The patient often becomes unconscious within 6 seconds. With every minute after an SCA, the chance of survival for the patient can incrementally decrease, as much as 10% per minute. For example, absence of oxygen for 2 minutes can lead to brain damage and if the absence lasts for more than 4 minutes, brain cells may be permanently lost. However, if oxygen supply is restored immediately, the patient can regain consciousness within seconds.

Treatment of sudden cardiac arrest (SCA) typically involves resuscitation with CPR and defibrillation. A defibrillator device, such as an automated external defibrillator (AED) or a wearable cardiac defibrillator (WCD), can be used to deliver a therapeutic dose of electrical energy through the chest wall to the heart of the patient. This can often restart the heart and restore the heart's natural rhythm. With prompt treatment, SCA can be reversible and at times, lead to a successful recovery.

Urgency in obtaining appropriate medical care for various medical events, heightens the need to quickly equip different support persons with relevant information about the situation of the patient. Easy access to information particular to the patient related to a medical event can quicken the time that the patient receives basic life support and other beneficial actions even before the patient arrives at a medical care facility.

SUMMARY

A medical support system (also referred to as "support system") is provided to facilitate prompt access to situation information by a support person who assists a patient experiencing a medical event that requires immediate attention. A wearable medical device (also referred to as "wearable article" or "wearable") gathers data that can be used in generating situation reports accessed on the fly by support persons. The medical support system may be able to adapt the situation reports to a variety of support persons who may be available to lend care to a patient at a time of need. The situation reports include critical health information regarding a patient for the medical event, such as lifesaving information regarding the situation of the patient prior to, during, and/or immediately after the medical event. Various rapid communication methods may be employed to quickly provide a support person with access to the situation report.

A method is provided that employs a medical support system to create situation reports and enable access to such reports in assisting a patient. According to the method, patient data may be gathered (e.g., generated or collected) by a wearable medical device worn by the patient. A determination is made by the wearable device that the patient experiences a medical event, such as one or more arrythmias, at a patient location that is away from a medical treatment site. Such determination may be based, at least in part on the gathered patient data. The wearable medical device may further initiate treatment protocols, such as defibrillation treatment, to address the medical event. At least one of a remote computing device and/or the wearable medical device generates a situation report that includes at least some of the patient data related to one or more occurrences associated with the medical event that satisfy one or more situation factors. A support person at the patient location is provided with access to the situation report during a critical time for care for use in caring for the patient during a critical time for care. Access to the situation report may be provided by at least one of a remote computing device and/or the wearable medical device.

In some arrangements of the method, the situation report may be generated by determining an event time period related to the medical event and/or the patient. In such cases, the situation factor(s) used in generating the situation report may include occurrences corresponding to the event time period. Patient data is identified as corresponding to the event time period. In some aspects, the situation report may include patient context information. Including but not limited to a prior patient activity level, a type of prior patient activity, a prior location of the patient, a patient current state or prior state, one or more vital signs of the patient, and combinations thereof.

The situation report may also be generated by determining a level of expertise of the support person. Expertise-appropriate situation information may be extracted from the patient data based, at least in part, on the determined level of expertise. The situation report may be adapted, at least in part, to the level of expertise.

In situations where the medical event includes one or multiple arrhythmias, the situation report includes at least one characteristic of the one or more arrhythmias and/or at least one characteristic of the defibrillation treatment. The situation report may include situation information from a group of: an onset time for each of the arrhythmias, a duration of each of the arrhythmias, a number of shocks delivered, a number of arrhythmias within an event time period, a type of each of the arrhythmias, and combinations thereof.

In some implementations, to provide access to the situation report, a webpage may be generated to include the situation report. Linking data to the webpage may be delivered via a rapid communication connection to a communication device of the support person. The rapid communication connection may include at least one process of presenting a scannable quick response (QR) code, broadcasting a BLE advertising packet including the linking data, sending radio frequency identification (RFID) signals with the linking data embedded, transmitting the linking data with near-field communication (NFC), and emitting a pattern of audio signals corresponding to the linking data. For example, delivering the linking data may include transmitting the BLE advertising packet having a universally unique identification (UUID) for a service that includes situation reporting for the medical event. In using such delivery methods, the support person may be authenticated to access a particular tier of detail provided in the situation report. A prompt may be presented to the support person to pair the support system with the communication device of the support person.

In still some aspects of the method, a type of the wearable medical device may be determined from, at least in part, header data in the one or more situation reports and/or patient data. The determined type of wearable medical device may be used in generating the webpage. Some methods of generating the situation report may also include determining a level of expertise of the support person and extracting from the patient data, expertise-appropriate situation information based, at least in part, on the determined level of expertise.

A medical support system is provided to perform the above described methods to create information reports for access in assisting a patient. The system includes a wearable medical device worn by a patient and configured to gather patient data. Such wearable medical device may include a patient assessment module to determine that the patient experiences a medical event, based at least in part on the patient data. In some implementations, the wearable medical device may also include one or more treatment components to deliver treatment for the medical event to the patient. The system further comprises at least one remote computing device having an interface for receiving the patient data from the wearable medical device and one or more processors and logic encoded in one or more non-transitory media for execution by the one or more processors. When executed, the logic is operable to perform steps. Such steps comprise generating by a data generator module, a situation report including information related to one or more occurrences associated with the medical event. Further steps may include providing by a webpage module, access for a support person at a patient location, to the situation report for use in caring for the patient during a critical time for care of the patient. In some configurations of the medical support system, a method is used that employs a Bluetooth low energy (BLE) connection to provide access to situation reports in assisting a patient. The wearable medical device may determine that the patient, who is away form a medical treatment site, is experiencing at least one medical event. The wearable device may be triggered by detection of the medical event to establish the BLE connection with a communication device of a support person. The detected medical event may encompass multiple related medical events occurring within an event time period.

In establishing the connection, a BLE advertising packet may be disseminated from the wearable medical device to advertise the medical event and advertise availability of a situation report for the medical event. The BLE advertising packet may be configured to be received by an application running on the communication device of the support person. A response may be received from the communication device requesting access to the situation report. The wearable medical device may deliver a BLE packet with linking data to a webpage to the communication device. The BLE packet may be included in the BLE advertising packet or a scan response packet. The webpage includes the situation report having patient data related to one or more occurrences associated with the medical event. Upon activation of the linking data by the communication device, access to the webpage may be provided to the communication device for the support person.

In some implementations, the BLE advertising packet includes a UUID for a service of providing the situation report. In still some cases, the BLE advertising packet may include patient spotting information at least one of patient location information and a physical description of the patient to assist in locating the patient.

Furthermore, in some configurations, the BLE connection may be bidirectional. A request for particular additional information in the situation report may be received from the communication device of the support person. In response, access may be provided to the additional situation information. In some cases, prior to updating the webpage, approval of the support person for high tier details in the situation report may be determined for the support person. The application on the communication device may be confirmed as indicating pre-authorization of the support person.

In some implementations, a method is provided that comprises in addition to collecting and/or generating patient data and determining a medical event as described above, respective levels of expertise of one or more support persons in a chain of care for the patient is also determined. The situation reports are generated from the patient data, as associated with at least one occurrence related to the medical event and based, at least in part, on the respective level of expertise. Each of the one or more support persons are provided with access to the situation reports adapted for the respective level of expertise of each support person.

Adapted situation reports may be generated by determining that the level of expertise of a first support person of the one or more support persons, meets a basic first threshold. Such basic situation report is generated using a first tier of situation information. Further, an advanced adapted situation report may be generated by determining the level of expertise of a second support person of the one or more support persons, meets an advanced second threshold. Such advanced situation report is generated using a second tier of situation information.

This summary is not intended to identify key features of the claimed subject matter, nor is it intended to be used as an aid in determining the scope of the claimed subject matter.

BRIEF DESCRIPTION OF THE DRAWINGS

Various implementations in accordance with the present disclosure will be described with reference to the drawings.

DETAILED DESCRIPTION

Figure 1:
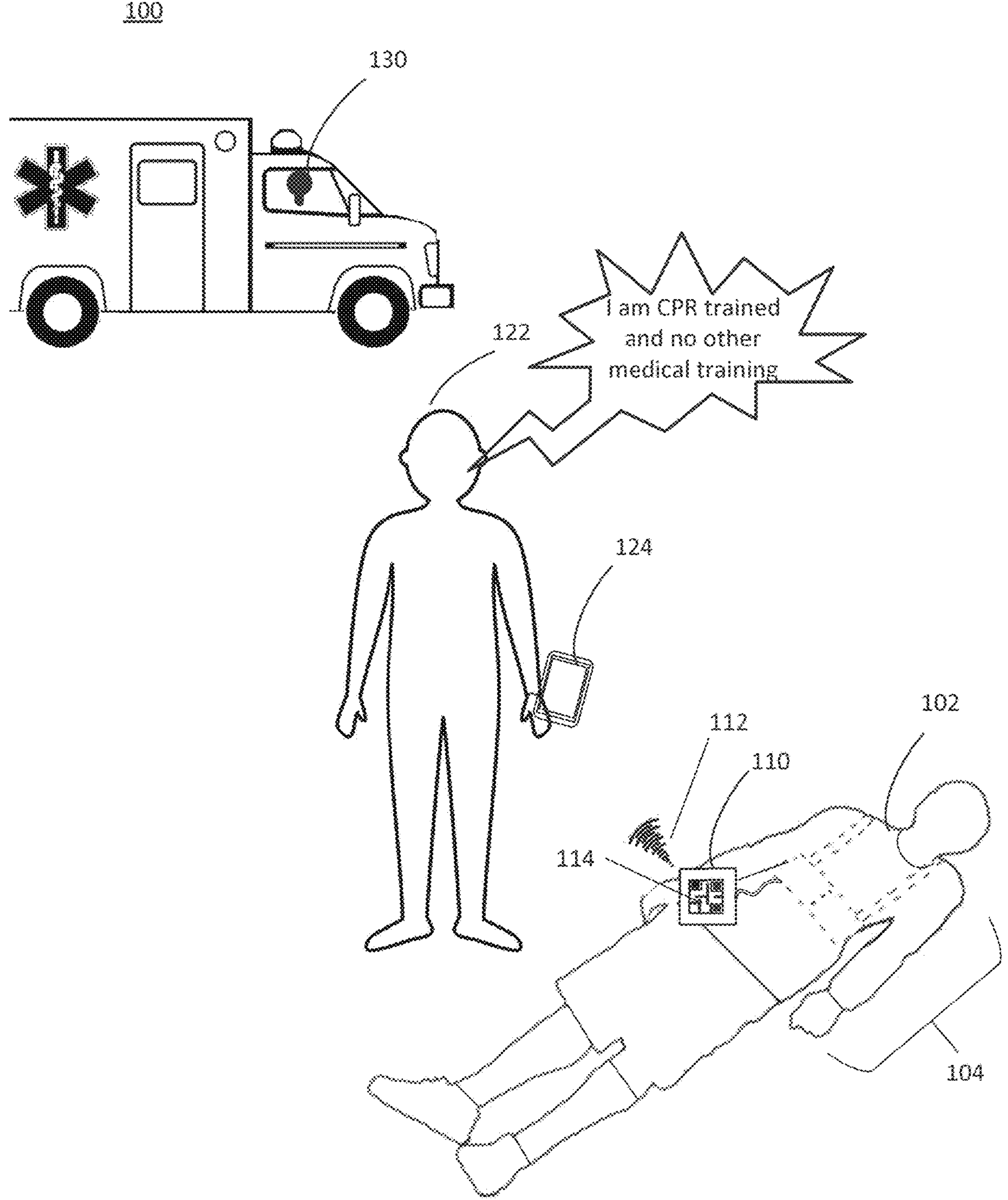
FIG. 1 is a diagram of an example of the medical support system employed in a chain of care for a patient experiencing a medical event, in accordance with some implementations.

In the following description, various implementations will be described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical support system provides a framework which can be tailored to individual systems built around the medical support system. Elements may be described in terms of "basic functionality" or varying degrees of functionality.

The present medical support system produces situation reports about a patient experiencing one or more medical events requiring a support person at the scene to provide care to the patient. The medical support system further provides mechanisms for rapid and convenient access to the situation reports by the support person to assist in performing appropriate care for the patient. The medical event can be an emergency that poses an immediate risk to the health, especially the long term well-being, or the life of the patient.

A wearable medical device that includes a wearable article worn by the patient, gathers patient data from which the situation reports are generated. The patient data may include various data related to occurrence(s) associated with the medical event. The occurrences may be a number of episodes of the medical event occurring close in time, environmental happenings around the time of the medical event, actions or state of the patient before, during or after the medical event, detection of various patient physiological parameters (such as a glucose level for a patient with diabetes), etc. The support system uses various situation factors to extract from the patient data, situation information associated with the medical event. The support system presents the situation reports to various support persons assisting the patient during a critical time for care.

At times, the patient may experience multiple related medical events, which may be connected by time of the occurrences falling within an event time period, cause and effect, various medical effects stemming from a common cause, or other relationships. For example, a medical event of a patient falling may be the result of another medical event of a cardiac episode. Situation information provided in the situation report may be associated with each individual related medical event and/or a relationship between medical events. In some implementations, situation information may provide the time between various related medical events and/or time between treatments for the related medical events.

In some implementations, situation reports are generated on the fly and adapted to the assistance that is currently available for the patient. For example, situation reports may be tailored according to a level of expertise of any given support person, such as an extent of experience and/or training of the support person. The situation report may also be adapted according to accessibility of resources by the support persons at the scene. The situation reports can be conveniently accessed by a support person on location. In some implementations, the support person may be authenticated to determine a level of detail for the situation report.

Situation information may reflect the situation of the patient immediately prior to the medical event, during the medical event, and/or immediately after the patient experiences a medical event. In some implementations, the situation information may include characteristics of the medical event, characteristics of treatment provided to address the medical event, patient context, environmental conditions, etc.

Access to situation reports may be controlled, such as a support person having a software reporting application running on a device that enables authorized communication with a server and/or wearable medical device to receive and/or view the situation report. At times, controlled access may enable a support person to gain access to a high (second) tier situation report that includes patient sensitive information, complex medical details, instructions on care that only a trained professional can perform, and other situation information appropriate for a trained and/or pre-approved support person. Controlled access via a software application may include BLE communication connection or other rapid communication connections with the medical device to obtain linking data to high tier situation reports or low tier situation reports. In some implementations, unrestricted access may be provided to any support person on the scene, for example, to convey low (first) tier situation report with simple information to perform basic life support on the patient appropriate for an untrained or limited trained support person. Rapid communication connections for unrestricted access may include scanning a QR code with a personal device of the support person. Connection with the remote computing device or other computing device to access the situation report may be via the reporting application or other connection mechanism. Additional tiers of situation reports are possible depending on the training level and/or authorization level of the support person.

The term "patient" as used in this description refers to a person who experiences a medical event or is suspected of experiencing a medical event. A "medical event" is a medical related problem or occurrence detectable by the wearable medical device and for which time sensitive care is required. For example, a medical event related to cardiac conditions may include ventricular tachycardia (VT), ventricular fibrillation (VF), bradycardia, supraventricular tachycardia (SVT), atrial fibrillation (AF), asystole, and non-sustained ventricular arrhythmia episodes, etc. Occurrences associated with a medical event may include a physical happening that is part of the medical event, such as an arrythmia, may include a symptom of a medical condition, and may also include a treatment provided to address the medical event.

The medical event can initiate at a first physical location, which is typically a non-medical treatment site, and can continue through a chain of care as the patient moves or is moved to other locations. For example, the patient may first experience the medical event while in a public place away from a medical treatment site, then be transported in a medical emergency vehicle, and arrive at a medical treatment site, such as a hospital. Thus, the term "patient location" of the medical event can include one or more physical locations. Various support persons in a chain of care at any of these patient locations may use the medical support system to gain valuable knowledge of the situation of the patient and multiple situation reports can be adapted to the different support persons and/or resources available at any given time along the chain of care.

A "rescuer" for purposes of this description, refers to a support person who had been previously formally trained in medical techniques to address the type of medical event of a patient. A rescuer can include an emergency medical technician (EMT), emergency room staff, doctor or other formally trained persons who are with the patient at the scene of the medical event or along the chain of care immediately after the medical event during the critical time for care.

A "bystander" for purposes of this description refers to a person at the scene of the patient location who is not educated in addressing the type of medical event that the patient experiences. The bystander is considered to be untrained or has limited training in medical techniques to deal with the medical event. A person who unexpectedly happens to be at the scene of the medical event and who has a high threshold level of training, may be considered a rescuer for purposes of determining a particular tier of detail provided in the situation report. However, such an on-the-spot rescuer may not have pre-authorization to access certain patient-sensitive information. As such, the situation report may include advanced treatment details but withhold certain patient identifying information. However, in some circumstances, a patient may provide pre-approval for any medical professional to access patient sensitive information during an emergency and the situation reports may include such patient sensitive information accordingly.

A level of expertise refers to an ability of a support person to provide a degree of care to a patient based, for example, on skill, training, education, certifications, age, and the like, or combinations, thereof, for the support person. The level of expertise may be assessed with reference to threshold expertise levels, such as basic, intermediate, advanced. Other systems of categorizing levels of expertise are possible, such as use of number values. Note that the terms "meeting" or "satisfying" a threshold, or variations thereof, as used in this description means a value being equal to and/or exceeding a predefined threshold amount.

Basic life-support (BLS) refers to fundamental medical care provided to a patient experiencing a potentially life-threatening or injury, illness, or condition before advanced life support can be provided. BLS can include cardiopulmonary resuscitation (CPR), Basic acts are typically able to be performed by an untrained or limited-trained bystander. Medical care provided by support persons using the present medical support system may implement BLS or other medical care needed to sustain or otherwise help a patient prior to availability of advanced life support.

A "critical time" for care can be any length of time after the onset of a medical event during which care of the patient may critically effect the outcome for the patient. For example, for a patient suffering from SCA the critical period may be just minutes before an irreversible health outcome happens to perform CPR treatment. The medical support system is configured to provide a situation report within the critical time for care of a patient.

In some implementations, a rapid communication connection may be established to transfer to a support person linking data that enables access to the situation report, e.g., via a server, saving precious seconds. The linking data may include a direct link such as a URL, or other data used by the reporting application to make the connection with the remote computing device or other computing device that provide access to the situation report. The linking data may be used by various support persons associated with any level of expertise to access an appropriate tier situation report, such as by an authorized rescuer to access high tier situation reports or by a bystander who accesses low tier (basic) situation reports. For example, rapid communication connection may include quick response (QR) code, BLE, near field communication (NFC), infrared communication (e.g., irDA), radio-frequency identification (RFID), communicating the link with Zigbee transmission, use of an acoustic encoded patterns, e.g., encoded QR code, or other audio data transmission techniques including audible QR code, and other instantaneous proximity-based data transfer techniques used by a support person to access the situation report. Use of such rapid communication connections could be faster for obtaining a link or uniform resource locator (URL) information than trying to call a medical system or manually entering a URL to a website to access the situation report.

For illustration purposes as depicted in FIG. 1, an example use case of the medical support system 102 includes a patient 104 suddenly experiencing a medical emergency at a non-medical treatment site 100. The medical event is detected by a wearable medical device 104 including a medical article worn by the patient 104. The medical event requires a bystander and/or rescuer to take an action to help the patient. In this illustration, the patient suffers an SCA. In other cases, various different medical events may be experienced by the patient 104 and assisted by the medical support system 102. According to this example, a bystander 122 at the scene of the medical event intends to assist the patient 102. The bystander 122 is not initially aware of the circumstances of the patient 102 or treatment provided by the wearable medical device. Without such background information, care for the patient would be limited and delayed. The bystander 122 may not be familiar with the wearable medical device, and any precautions a bystander or rescuer may need to take when touching or approaching a patient wearing the wearable medical device. The bystander gains the needed information in a situation report and is able to perform appropriate basic life support actions.

In this illustration, the medical support system provides a voice alert via a speaker 112 on a main unit 110 of the wearable device 104 to let the bystander 122 know the particular medical event the patient is experiencing. The voice alert may also convey that situation report information is available to assist the bystander in caring for the patient. In other examples, the bystander may be alerted that a patient is in need of help, via other output mechanisms in addition to or instead of an audio alert, such as an alert displayed on the wearable medical device or a rapid communication connection from the wearable medical device to a mobile communication device 124 of the bystander. The bystander may be given an option to view a situation report displayed on a screen of the wearable medical device or view the situation report on the mobile communication device 124 of the bystander, along with instructions on accessing the situation report.

The bystander communication device 124 may be a smartphone, smart watch, specialized medical device, such as a defibrillator enabled for communication with the wearable medical device, etc. At times, a bystander may have a particular level of expertise in addressing the type of medical event experienced by the patient. The support system may prompt the bystander to enter expertise information into the system, such as via the mobile communication device of the bystander or display screen of the wearable medical device. The level of expertise information is compared to a threshold level of expertise by the support system to determine a tier of situation information appropriate for the bystander to access.

In some cases, the voice alert may prompt the bystander to input by speech, a description of medical expertise the bystander has in order to care for the medical event of the patient. The bystander 122 speaks into a microphone of a patient communication device (not shown), main unit 110 of the wearable device, or other device having a microphone. In some implementations, Authentication for accessing the tier of situation information may be preestablished for the support person or provided via a reporting application running on the communication device of the support person. View of a situation report may be adjusted based on the level of expertise to access a particular tier of situation information. For example, once authenticated for a tier of situation information, a link, e.g., URL, that is specific for the tier of information may be provided to the authenticated support person.

The bystander 122 may hold the mobile communication device 124 close to the main unit 110 of the wearable medical device 104 and scans a QR code 114 shown on the medical device 104, such as on a sticker or displayed on a screen of the main unit 110. Resolving the QR code with the mobile communication device 124 can open a web page or other data format that includes the situation report with situation information. Other rapid communication connections may be employed as well.

The medical support system may provide the bystander 122 with a situation report having a first tier of situation information appropriate for a basic level of expertise. The basic first tier of situation information may also be used as a default tier when the support person is unverified as having a particular level of expertise in addressing the medical event and/or unauthorized to receive a higher tier of situation information.

The first tier situation report may include details about occurrences related to the medical event, for example, basic details about the medical event, treatments being performed by the wearable medical device, basic life support instructions, etc. The first tier situation report may exclude situation information reserved for support persons with higher expertise, such as restricted patient identifying information, treatment instructions that require higher levels of medical expertise, patient characteristics and/or details about medical event occurrences that are only beneficial for support persons having higher expertise, other sensitive patient data, etc.

In some implementations, the first tier situation information may include patient specific information, for example, critical information in view of the medical event and/or patient. For example, where a preexisting condition of the patient renders certain actions deleterious for the patient, such as an allergic reaction or actions that may negatively implicate secondary medical conditions of the patient, the bystander may be warned not to perform such actions. Where basic care is critically necessary for the particular patient, such as use of an EpiPen or providing a sweet food to address a diabetes attack, the bystander may be instructed to perform including instructions on the steps needed to perform the critically necessary basic acts accordingly.

The first tier situation information may exclude patient personal information, such as person identifying information, and other sensitive information regarding the patient. Further excluded from first tier information may be medical details that require a trained person to use in providing medical care to the patient.

If a treatment episode has recently been delivered or is about to be delivered to the patient by the wearable medical device to address the current medical emergency, the first tier information may notify the bystander of the treatment episode. For example, should a shock treatment still be required, the screen depicts situation report information to inform the bystander that a shock treatment will be delivered to the patient and to stand clear. The wearable medical device may then deliver a therapeutic shock to the patient and the medical support system then informs the bystander that CPR can be initiated, such as providing instructions for chest compressions and recue breaths.

In the illustration in FIG. 1, an EMS rescuer 130 is subsequently on the scene of the medical emergency as a trained rescuer support person who is authorized to access advanced second tier information including personal sensitive information of the patient. Without the situation information provided by the support system, crucial time would be taken by the EMS rescuer 130 in assessing the situation of the patient before tending to the needs of the patient. A rescuer may be a trained person meeting a high threshold level of expertise, which may be set based on the medical event being addresses.

The EMS rescuer 130 is authenticated as having a high threshold level of expertise and/or authorized to access personal information of the patient. The EMS rescuer 130 has a near field communication (NFC) enabled device that includes a unique NFC tag readable by an NFC reader of the wearable medical device. In some implementations, the wearable medical device may be triggered to scan for the NFC tag upon detection that the patient experiences a medical event requiring intervention by the support person. At other times, the NFC scanning mechanism may remain dormant. In this manner, battery life of the wearable medical device may be preserved for times in which a support person is needed. For example, the rescuer may be prequalified at a high level of expertise and may have pre-installed the NFC tag consistent with the high level of expertise onto a personal communication device of the rescuer. In other implementations, the rescuer may have another dedicated item that includes the NFC tag, such as a wristband, card, badge, key fob, token, etc.

The EMS rescuer 130 pairs the NFC tag with the wearable medical device to enable authorized access to second (high) tier situation information, which can include patient sensitive information. For example, the EMS rescuer 130 is provided with identifying information to identify the patient and other patient-specific personal information, such as name, address, medical history including prior medical events and other medical conditions of the patient, emergency contact, advanced characteristics of the medical event detected by the wearable device. Second (high) tier information may also include patient context information for details of the patient within an event time period considered relevant to the particular medical event. Patient context information may include, for example, occurrences of: patient activity prior to the medical event, a prior patient activity level (such as high heart rate exercise), a type of prior patient activity (such as a type of exercise), a prior location of the patient, a patient current state or prior state (such as hydration level, time since last meal, lack of sleep, stress level, etc.), one or more current and/or prior vital signs or other physiological parameters of the patient, and combinations thereof, etc. In some implementations, select vital sign data, such as vital sign data associated with a particular time or corresponding with other patient detected events, may be extracted from streamed medical data, such as stream of ECG data. The stream of medical data may be continuously captured and collected via sensors of the wearable medical device. In other implementations, the data ma vital sign may be captured at defined intervals or upon triggering of an event. Patient context information may also include a comparison of patient data of the patient. The EMS rescuer 130 may also have access to the situation information in the first tier situation report that is available to the bystander.

Benefits of the medical support system include improving patient care by a support person. Proactively providing of situation report information may reduce the time to diagnosis, free up more time for care, and allow for appropriate treatment specifically tailored to the medical event and patient situation.

Some implementations of the medical support system may additionally present instructions for appropriate actions by a support person, especially in cases that the support person is unknowledgeable on ways to help the patient. For example, instructions on precautions may be presented when touching or approaching a patient wearing a wearable medical device. The support person may not be aware of that the wearable medical device may deliver a treatment that requires careful interaction by the support person. For example, a wearable medical device that delivers a shock could injure the support person if touching the patient. In another example, a patient may have psychological disturbances that may be aggravated if the support person interacts with the patient in a particular manner. Instructions may also be provided on how to handle the wearable medical device when taking basic life support actions (e.g., whether and/or how to remove/disable the wearable medical device when applying an (AED), advanced life support (ALS) defibrillator, or automated CPR machine).

Figure 2:
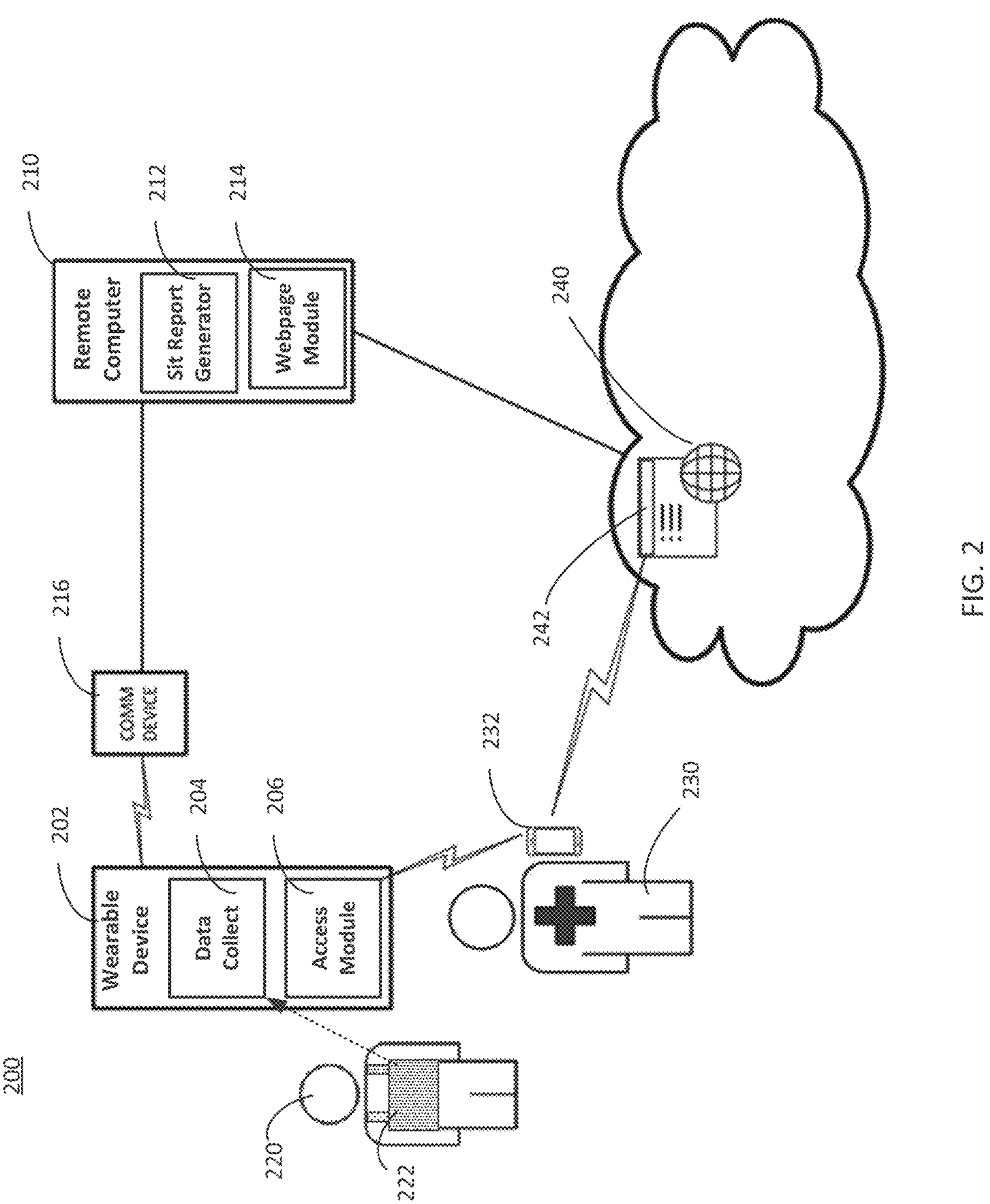
FIG. 2 is a schematic diagram of example of the medical support system including components that interact via a network, in accordance with some implementations.

FIG. 2 shows the medical support system 200 having components including a wearable medical device 202 including a wearable medical article 222 that is worn by patient 220 and a remote computing system 210, which interact over a network 240. The medical support system 200 refers to one or more physical devices and also includes software components. The wearable medical device includes functional computing components, such as one or more processors, one or more memories, interfaces, operating system, computer programs, etc., similar or the same as such computing components described regarding the remote computing device 700 in FIG. 7.

Particular implementations of various computing components of the medical support system, e.g., remote computing device, wearable medical device, etc., may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular implementations. For example, a non-transitory medium such as a hardware storage device can be used to store the control logic, which can include executable instructions.

Some examples of a wearable medical device 202 include a wearable cardioverter defibrillator (WCD), such as the ASSURE wearable defibrillator system available from Kestra Medical Technologies, Inc., Kirkland, WA. Other WCD devices are possible for use in the medical support system. A WCD may also provide pacing therapy for detected bradycardia and/or asystole. The wearable medical device may further include monitoring devices that check patient parameters with or without integrated treatment components, such as Wearable Cardiac Monitoring system (WCM) by Kestra Medical Technologies, Inc., Kirkland, WA, Holter type of monitors, mobile cardiac outpatient telemetry (MCOT) systems by Philips Company, etc. Other wearable medical devices may be employed in the medical support system to address a variety of medical events and medical conditions. An example wearable medical device is described below with regards to FIG. 6.

The wearable medical device 202 includes a wearable medical article 222 (also known as a wearable article or support structure). The wearable article 222 can be implemented in many different ways. For example, it can be implemented in a single component or a combination of multiple components. In embodiments, the wearable article 222 could include a vest, a half-vest, a garment, etc. In such embodiments such items can be worn similarly to analogous articles of clothing. In embodiments, the wearable article 222 could include a harness, one or more belts or straps, etc. In such embodiments, such items can be worn by the patient around the torso, hips, over the shoulder, etc.

In embodiments, wearable article 222 can include a container or housing. In such embodiments, the support structure can be worn by being attached to the body of the patient by adhesive material, for example as shown and described in U.S. Pat. No. 8,024,037. The wearable article 206 can even be implemented as described for the support structure of U.S. Publication No. US2017/0056682, which is incorporated herein by reference. Of course, in such embodiments, the person skilled in the art will recognize that additional components of the wearable medical device 202 can be in the housing of the wearable article 222 instead of being attached externally to the wearable article, for example as described in the U.S. Publication No. 2017/0056682 document. The wearable article be other forms of wearables such as a headgear, wrist band, ankle band, etc. There can be other examples as well.

Software components of the wearable medical device 202 include a patient data gathering module 204 to compile patient data generated and/or collected by the wearable medical device 202 and an access module 206 to enable a support person to access a situation report. The data gathering module 204 and access module 206 may be implemented as software components stored in a memory of the wearable medical device 202. Other wearable device components may include a connection interface (such as an interface port) for the wearable device to interface with a communication device of the support person.

Patient data may be regularly collected or generated by the wearable medical device 202 while the patient goes about day-to-day activities. This patient data is assembled by the data gathering module 204 for transfer to the remote computing system 210. Patient data is associated with the overall health of the patient and includes data related to the current medical event as well as other data unrelated to the medical event.

Some patient data may be generated by the wearable medical device 202 by a variety of sensors that may be integrated with or connected to the wearable medical article 222 or otherwise in communication with the wearable medical device. Examples of patient data from sensors or devices integrated with or in communication with the wearable device may include patient circumstances data, such as ECG data by electrodes of the wearable device, temperature of the patient and/or environment of the patient by a thermometer, peripheral capillary oxygen saturation (spO2) of the patient by an oximeter, step count data for the patient; respiration data measured by the wearable device; pulse ox data measured or collected by the wearable device, accelerometer data, which can indicate, for example, that the patient has fallen, or has been unconscious for a significant period of time, time records by a clock, a global positioning system (GPS) to indicate patient location and prior travel routes, etc. Patient data may also include characteristics of the medical event, such as description of a fall, nature of a seizure, etc. Details about various sensors of the wearable medical device 202 is described below with regards to FIG. 6. There can be other types of patient data generated by the wearable device from other types of sensors or detection device sources.

Patient data generated by a wearable medical device may include data related to treatment/therapy provided by the wearable device or diverted (e.g., initiated by the wearable device but failed to be provided to the patient) for the current instance of the medical event. For example, patient data may include asystole, description of types of treatment actions, e.g., shock deliveries and timing/number of treatment actions pacing deliveries, non-performed treatments due to diversion by the patient (e.g., the patient overriding the commencement of the treatment), etc.

Some patient data may be received by the wearable medical device 202 from sources external to the wearable device 202. Some of this patient data may be tangentially related to the medical event and relevant as situation information for a support person. Patient data from external sources may include patient history data, such as from previous medical events of the patient, other patient conditions, disabilities, and/or characteristics, patient emergency contact, cautions that certain treatments are to be avoided for the particular patient, location tracking data, etc.

In some implementations, the wearable medical device 202 may regularly transfer data to remote computing system 210, such as transferring the data at a prescheduled time. In some implementations, the patient data may be transferred according to a trigger event, such as detection of the medical event by the wearable medical device 202. Such trigger event may include the data gathering module or other alert module of the wearable medical device causing the transmission of the patient data 204. In some implementations, transfer of patient data may occur according to a manual request, such as the patient and/or support person activating a send command. In some medical support systems, any or all of the foregoing transfer techniques may be employed.

Transfer of the patient data to the remote computing device 210 may occur using any of a variety of data communication mechanisms. At times, the wearable medical device 202 transmits the patient data to the remote computing device 210 via a communication device, which can be a wireless communication link, e.g., WiFi or cellular, to a patient communication device 216 of the patient. The patient communication device 216 may be a dedicated device for the sole use or major use in the medical support system. In other implementations, the patient communication device 216 may be a general device, such as a mobile phone, which includes software configured to transfer patient data to the remote computing device or some intermediary device that then transfers the patient data to the remote computing device 210. In still some implementations, the communication device 216 may be integrated in the wearable medical device 202 and include wired communications with the processor and memory of the wearable device 202 to transmit patient data to the remote communication device 210.

In some circumstances, raw patient data in a basic format as provided directly from data sources may be preprocessed by the wearable medical device 202 prior to transferring the patient data to the remote computing device to create the situation reports. As such, multiple stages of processing may be performed on the patient data by the wearable device 202, the remote computing device 210, and/or other intermediary devices, to create situation information for situation reports. For example, the wearable device 202 may create a summary of a medical event including characteristics of the medical event, e.g., arrhythmias, such as the number and/or types of each occurrence of the current medical event, e.g., each arrhythmias of detected, the time and duration of each detected occurrence, etc. In some implementations, location tracking data may be used to map the path or route the patient traveled just prior detected medical event. Step count data during a predefined prior period of time before the detected events may be assessed as an indication of whether the patient was active or inactive just prior to detected events. However, in some implementations, some patient data may be extracted from the corpus of patient data and included in the situation report, as is, without any processing of the patient data.

The remote computing device 210 can be a server or other portal. An example of such a remote computing device 210 is KESTRA CARESTATION, from Kestra Medical Technologies, Inc., Kirkland WA. Other computing devices 210 may be employed configured to receive patient data, formulate situation reports from the patient data, and transfer the situation reports to a receiving point at the patient location for a support person to access. The remote computing system 210 may be implemented as a server, or using a web service such as, for example, Amazon Web Services (AWS) available from Amazon or Azure available from Microsoft. The remote computing device may also include multiple computer devices, such as on a cloud system, in which tasks may be distributed between computing device. In some cases, a patient location, such as a GPS location of the patient, may be published by the wearable device to a service that monitors for patients in needs of immediate patient care outside of a medical facility. Such patient monitoring computing devices may coordinate with the support person and a remote computing device that generates the situation report to perform access to the situation report. Thus, the term "remote computing device" may include one or more computing devices that are remote from the site of the patient and work to support generation, availability, and access of the situation report.

The remote computing device 210 includes a report generation module 212 and, in some implementations, may also include a web module 214, both of which may be implemented using software modules stored in a memory of the remote computing device 210 and executed by one or more processors of the remote computing device 210.

The report generation module 212 produces situation reports that includes situation information extracted from the patient data associated with the medical event. The report generation module 212 packages the situation information into an easy to read structure to assist a support person in caring for the patient. The patient data used to produce situation information can be a collection of data received from the wearable device 202 as well as patient data received from other sources, such as a data stored in the remote computing device 210 or patient data received from other external data repositories, data entered by a person, such as a medical professional, contact person of the patient, etc.

As described above, the report generation module 212 receives patient data (e.g., raw data detected by sensors of the wearable device). Patient data may be processed by extracting patient data relevant to the medical event and potentially helpful for a support person, and putting it into a form that is easily recognized by the support person in caring for the patient. Such relevant information may include characteristics of the medical event, characteristics of any treatment already provided or soon to be provided by the wearable device, characteristics of the patient, instructions on how to care for the patient, warnings on actions not to be taken or needed to be taken by the support person, etc. For example, situation information related to a cardiac arrythmia event may include an onset time for each of the arrhythmias, a duration of each of the arrhythmias, a number of shocks delivered, a number of arrhythmias within an event time period, a type of each of the arrhythmias, and combinations thereof. Situation reports include data extracted from or otherwise processed based on the patient data that is determined to be relevant to the current medical event by meeting one or more situation factors. In some cases, a pattern of the patient data may be identified as an indication of pertinent situation information to assist in caring for the patient.

The situation factors used in the processing of the situation information may depend on characteristics of the medical event, e.g., type of event. For example, situation factors may include an event time period relative to the medical event, identification of conditions that are known to induce or aggravate the medical condition, past patient history, etc.

The event time period may be defined according to the type of medical event and/or characteristics (e.g., patterns of behavior) of the patient to include a stretch of time applicable to the occurrence(s) of the medical event. For example, a diabetic medical event may be associated with an event time period of hours or a day to include food consumption. In this example, if a patient characteristically eats at particular times, the event time period may be defined accordingly. By contrast a cardiac medical event may have a shorter event time period to encompass more of the immediate happenings of the patient. For example, situation information may be extracted from ECG patient data for each medical event represented in the ECG data that meets threshold criteria for the event and results in an episode being opened. Some examples of recording of medical event episodes is described in U.S. Publication No. 20230091743, "Health Data Management and Display" filed Sep. 22, 2022, the contents of which is incorporated herein by reference.

In some implementations, the report generation module 212 may be configured to determine the type of wearable medical device 202, for example from header data that the transmitting wearable medical device includes in the patient data. In such cases, a header attached to the payload before transmission may include a classification of the wearable medical device that describes the patient parameter(s) being monitored, treatment provided by the wearable device, product number, serial number, and other identifying information. In some implementations, the remote computing device may cross reference the header data with a type of medical device. The report generation module 212, based on the determined type, can generate a situation report file appropriate for the type of wearable medical device. For example, a situation report file for a wearable device that solely monitors patient parameters would not include situation information related to treatment by the wearable medical device.

In some implementations, the situation report may be specifically adapted for a level of expertise determined for the support person, as described in detail below with regards to FIG. 4. In these cases, the level of experience of a support person at the scene may be a factor used in the processing of the patient data. For example, prior activity level of the patient may be useful for a rescuer and not as relevant for care by a bystander. Various tiers of detail may be extracted from the patient data depending, at least in part, on the level of experience of a support person. In this manner tiers of detailed situation report may be generated tailored to a The report generation module 212 can be configured to receive the patient data from the wearable medical device 202 (e.g., via the communication device 216) and process it into a situation report file that is provided to or accessed by the web module 214 or other module, such as an audio translator with text to speech functionality, to present the situation report to the support person. In some embodiments report generation module 212 is configured to automatically send the situation report file to the web module 214, while in others the report generation module 212 automatically sends a notification, a command, flag, or the like, to the web module 214, which causes the web module 214 to access the situation report file.

In some implementations, the report generation module 212 may be configured to analyze the received patient information to extract the event times, event summaries, ECG data for episodes, accelerometer, pulse ox, step count, patient location tracking maps, etc. of the patient just prior to detected events. Processing of the patient data to create the situation report may also include de-identifying the data to prevent access by support persons not authorized to access the identifying information. In some implementations, the report generation module 212 can be configured to analyze the received patient data to determine appropriate actions for the current medical event and provide prompts or pointers to prompts for these actions.

In some embodiments, each medical event type may serve as an index to a look-up table, library, or other database, that contains predetermined support prompts for various types of medical events. For example, support prompts could include instructions for performing CPR, providing a "metronome" for the CPR compression rate, positioning the patient to help prevent the patient from entering shock, check for bleeding, for example if a patient fall was indicated by the patient data, etc.

The webpage module 214 of the remote computing device 210 receives or accesses the situation report file from the report generation module 212. In some implementations of the medical support system 200, webpage module 214 is configured to format information from the situation report file for display in a webpage, such as converting the situation report file to an HTML page, a CSS document, or an image.

In some implementations, the situation report may be provided across multiple webpages and/or with links to some of the situation information. The webpage may include text, image(s) and/or video(s). The webpage may be assigned a URL to be accessed by the support person, for example, by scanning a QR code, such as by a software application running on the communication device 216 that has requested the situation report file, etc.

In some implementations, the webpage 242 may be unique to the wearable device 202 and/or to the current patient 220, accessible with a unique link, e.g., URL. In some such implementations, the web module 214 can be configured to determine the webpage 242 corresponding to the wearable device 202 and/or patient 220. The patient may be identified by patient identifying data included in the patient data by the wearable device 202. A link to the webpage, e.g., URL to the webpage and/or other webpage identifying information such as the IP address of the webpage, can be included in the situation report file by the report generation module 212.

In some implementations, the webpage module 214 may include logic to determine whether the situation report file is for a support person having a particular level of expertise, such as a bystander or a rescuer such as an EMT. For example, the webpage may display a prompt asking persons accessing the page to first indicate whether they are a bystander or a trained rescuer. Based on the indication provided, the webpage module 214 may be configured to display a page with instructions/prompts suited for the support person to perform the basic life support actions.

The access module 206 of the wearable medical device 202 provides one or more mechanisms for a support person 230, such as a bystander and/or rescuer, to access the situation report that can be in the form of the webpage 242 or other formats. The access module 206 may facilitate remote communication connections (for example, providing a QR code, BLE, NFC, infrared communication (irDA), RFID, communicating the link with Zigbee transmission, acoustic QR code or other audio data transmission techniques including audible QR code) with the communication device of the support person by formatting and encoding data into packets, signals, and other transmission modes.

Other formats of situation report may include a hands-free verbal recitation of the situation report. In such circumstances, the access module 206 can provide interactive access to situation information in which the support person 232 may request via a microphone of the wearable device, particular information from the situation report and the access module outputs the requested situation information through a speaker of the wearable device. The access module 206 can be implemented using a software module stored in a memory of the wearable medical device 202 and executed by one or more processors of the wearable medical device 202.

In some cases, the steps of providing access to the situation report may be distributed between the remote computing device 210 and the wearable medical deice 202. In some implementations, the access module 206 may be disposed in the remote computing device 210 in addition to, or instead of, the access module 206 being at the wearable medical device 202.

In some implementations, the access module 206 enables access to the situation report via a personal communication device 232 of the support person 230. Some mechanisms to get access via the personal communication device 232 includes a QR code displayed on the wearable device 202. For example, the QR code may be presented on a label on a component of the wearable medical device, a screen on an electronic component, etc. The QR code may be identified with a title such as: "Access the situation report for this patient using this QR code". Other labeling can be used in other deployments of a QR code.

The access module 206 can implement various mechanisms for the support person to access the situation report. In some implementations, BLE packets may be dispersed upon detection of a medical event and the communication device 232 may receive the BLE communication to establish a rapid communication connection with the support system. In some implementations, audio and/or visual prompt may be issued, such as through a user interface of the wearable medical device 202 to instruct support persons on how to access the situation report. For example, the access prompt may instruct the support person 230 to press a button of the wearable device 202 to pair with the personal communication device 232 (e.g., smartphone) of the support person 230 so that the wearable device 202 can transmit the situation report file to the communication device 232. The prompt may also instruct the support person 230 to provide a verbal response to display the situation report on a display of the wearable device 202. The prompt may instruct the support person 230 to scan the above-described QR code. In still other implementations, the access module 206 may interface with another computing device that enables access to the situation report. Other access and communication mechanisms are possible.

In some implementations, a situation report may be transmitted by the remote computing device 210 to the patient communication device 216. For example, the patient communication device 216 may be configured to transmit situation information to the remote location (as described above), as well as receive the situation report to present to the support person 230. In such cases, the prompt may instruct the support person 230 to use the patient communication device 216 to access a stored copy of the situation report. In some implementations, the patient communication device 216 may have a software application that is activated to display the situation report automatically when the patient communication device receives the situation report from the wearable device 202. Various combinations of one or more of the foregoing access prompts may be employed by the medical support system 200.

The network 240 may be used to transfer data and information between the various medical support system 200 components, such as between communication device 232 and remote computing system 210 and between remote computing system 210 and communication device 232. Other devices of the support system 200 may also use network 240 to communicate.

Network 240 may include one or more WANs (Wide-Area Networks) and/or LANs (Local-Area Networks), which may be wired and/or wireless. In some examples, the network 240 may include the Internet and/or one or more cellular networks, among other networks. For example, the network 240 may provide a connection, for example, through a local network to a host computer or to data equipment operated by an Internet Service Provider (ISP). The ISP in turn provides data communication services through the world wide packet data communication network (the "Internet").

The network 240 may operate according to one or more communication protocols, such as Bluetooth™, LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols.

Although the network 240 is shown as a single networks, it should be understood that the network 240 may include multiple, distinct networks that are themselves communicatively linked. The network 240 could take other forms as well.

The depictions in FIG. 2 is not to be construed as limiting components of the medical support system 200 and how the support system 200 is implemented. The medical support system 200 can be implemented in different ways with additional or less devices. For example,—in some implementations, the wearable medical device may be configured to create situation reports locally with a local situation report generator 212. For example, the wearable medical device may also or instead of the remote computing device, include the situation report generator to process the patient data, extract situation information, and create situation reports, and provide access to the situation reports to support person (s), without the need to use the remote computing device or such various of these steps may be distributed between the wearable medical device and the remote computing device. In some implementations, the wearable device may generate the situation report and communicate the situation report file to the remote computing device to produce a webpage that includes the situation report with webpage module 214.

Figure 3:
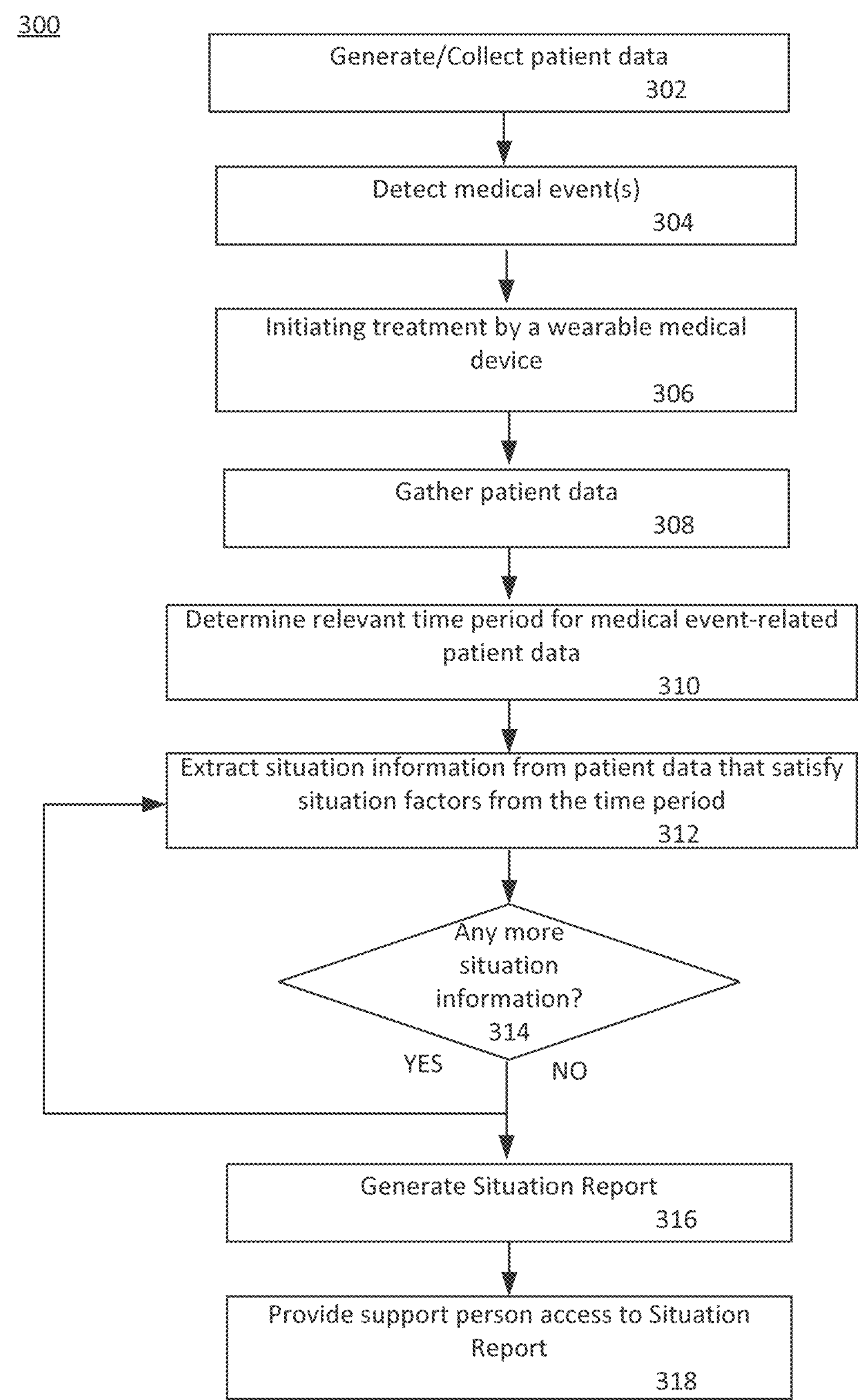
FIG. 3 is a flowchart of an example of a medical support process for generating situation reports for access by support persons, in accordance with some implementations.

FIG. 3 shows a flowchart of an example medical support process 300 to create situation reports for access in assisting a patient. In some implementations, the support process can be implemented on one or a combination of various computing devices, such as a mobile device application, e.g., client computing device, and/or an application running on a dedicated server, e.g., remote computing device, and/or an application hosted in the cloud. In implementations, the device or devices implementing the medical support process can be stand-alone or a combination of mobile processing and cloud processing.

In block 302, patient data are gathered, e.g., collected or generated, that are related to overall health of the patient that include data relevant to the medical event as well as data unrelated to the medical event. Typically, patient data are routinely and automatically collected by the wearable medical device as the patient wears the wearable article. By contrast, patient data may not solely comprise data generated or collected when a health event is detected. The patient data thereby includes data from prior to the detection of the health event. In some implementations, a portion of the patient data (but not all the patient data collected) may be gathered in response to detection of the health event. For example, specific sensors may be activated upon detection of the health event and patient data from such event triggered sensors may be collected along with other patient data.

In block 304, the wearable medical device detects a medical event being experienced by a patient. Various patient data including data, such as ECG's, from various sensors are assessed to determine a medical event is occurring for the patient. At times a combination of patient data is used to make the determination of a medical event. Examples of detecting medical events via a wearable device is described in U.S. Publication No. 2023/0071214, "Multi-Function Wearable Monitoring System With Sleep Disorder Warning, filed on Sep. 2, 2022, the contents of which is incorporated herein by reference.

In some implementations, in block 306, in response to the detection of the medical event, the wearable medical device provides treatment of the medical event to the patient. Treatment by the wearable device may include various levels of care to the patient and the medical event. Treatment may include life-sustaining actions by the wearable device, actions that maintain patient health until further help arrives, actions that address one aspect of the medical event but not all needs of the patient, etc. Along with the treatment provided by the wearable medical device, additional care is typically required to be administered by a support person. At times, treatment provided by the wearable device may continue during support person intervention.

Some medical support systems may skip the treatment step in block 306 and instead proceed to the step in block 308 in which patient data is gathered. For example, some wearable medical devices are configured for only monitoring patient parameters and not provide treatment. Other wearable devices may generally provide treatment for other medical events and are not configured to treat the current medical event.

In block 308, gathering of patient data includes generation of patient data by the wearable device as well as the wearable device collecting data from external sources. At times, gathering of the patient data includes pre-processing the patient data in a manner to support the detected current medical event, the support person available, etc. The patient data, in pre-processed or raw forms, are typically transferred from the wearable medical device for processing of situation information, generation of situation reports, and/or creation of a webpage or other access format.

In block 310, an event time period for medical event-related patient data may be determined. The event time period may depend, at least in part, on the nature of the medical event. For example, for a sudden cardiac event, a shortened time period immediately prior to the detection of the medical event may be pertinent, e.g., 15 minutes prior to detection of the medical event. For a medical event that characteristically builds over time, such as a diabetes emergency, the event time period may be extended, such as hours before the medical event.

In block 312, situation information is processed, e.g., extracted, put into context, and/or formatted, from patient data that satisfy situation factors including patient data from the relevant time period. Some patient data used for situation reports may be time-independent data, e.g., prior medical history of the patient, known patient characteristics, such as disabilities, sensitivities, etc. The relevant situation information may include patient context during the event time period. For example, a prior patient activity level, a type of prior patient activity, a prior location of the patient, a patient current state or prior state, one or more vital signs of the patient, and combinations thereof.

The situation factors may include one or more patient attributes or characteristics, characteristics of the medical event, and/or one or more characteristics of the wearable medical device. In some implementations, a type of the wearable medical device may be determined from by header data in the situation information. For example, a webpage having the situation report may be based, at least in part, on the type of the wearable medical device.

The situation factors may also include availability of the support person(s). For example, the support system may prompt the support person to input responses to availability questions, such as availability of tools/equipment that can help in the care, number of support persons available on the scene, etc. In this manner, the situation report may be adapted to the resources at the disposal of the support person. The medical support system may use natural language processing to discern the answers of the support person.

In decision block 314 it is determined whether there is more situation information to be used in the situation report. For example, if there is additional patient data needed for the report during the time period, the additional situation information is processed. If there is not further situation information, the situation report is generated in block 316, otherwise, the process returns to block 312 to extract/process the additional situation information.

In block 318, access to the situation report is provided to the current support person caring for the patient. For example, access may be provided via access module 206 described above with regards to FIG. 2. Modes of accessing the situation report may include visual display on a screen of various devices such as the wearable device, a patient communication device, a personal communication device of the support person, etc. The mode of communication may also be in audio form through a speaker of the wearable device, a patient communication device, a personal communication device of the support person.

The mode of access may vary depending on a variety of possible mode factors, such as the level of expertise of the support person, availability of devices to receive the situation report, environmental conditions such as time of day (e.g., night time access may be via audio reports) and patient location (e.g., visual reports may be used if there are loud interfering noises in the patient location). Mode factors may further include a particular mode requested by input of the support person, authentication of communication device of the support person, the specific medical event experienced by the patient, for example the instructions may be provided by audio if actions of the support person requires hands free attention to the patient, etc. In some implementations, a standard default mode of access is provided for each support person, such as display of the situation report on a screen of the wearable device or personal communication device of the support person.

In some implementations, the way that the reporting application connects the remote computing device and/or the webpage may control the different tier of situation information that is viewable in the situation report, such as a certificate used by the reporting application that specifies a tier of situation information appropriate for the support person. In still some implementations, in order for a support person to gain access to an advanced (high) tier situation report, the support person may be required to satisfy an identification verification, such as enter a password into the medical support system, satisfy a biometric authentication (e.g., scanning of fingerprint, facial recognition, iris recognition, etc.), input answers to security questions, scanning a badge, card, or other article having a security object, etc. Such security inputs by the support person may be compared to stored data previously registered with the medical support system. In some implementations, once a support person has been authorized to access a particular tier of situation report, a reporting application is installed on a personal communication device. In some implementations a reporting application identifies a level of preauthorization for the support person and communicates the preauthorization to the wearable medical device and/or remote computing device of the medical support system. At times, preauthorization is for an organization that the support person belongs rather than the individual, such as a medical service group registered with the medical support system.

In some implementations, authentication of the support person may be made by authentication of the communication device of the support person. The communication device of the support person may be a personal device, such as a smartphone, smart watch, tablet, etc. Authentication may be made via a certificate of the reporting application, which may be activated by pairing of the communication device with the wearable device, such as via a rapid communication connection. In other situations, the communication device may be a dedicated device for a level of experience support person carried by the support person to pair with or otherwise communicate with the medical support system.

In some implementations, a quick response (QR) code may be presented to a support person, such as displayed on a screen of the wearable device and/or communication device of the patient. The QR code, when scanned by a communication device of the support person, may enable access to a webpage that is generated to include an appropriate situation report. Other rapid communication connections may be used, such as an NFC tag scanned by the wearable device, BLE connections as described with regards to FIG. 5, etc.

Figure 4:
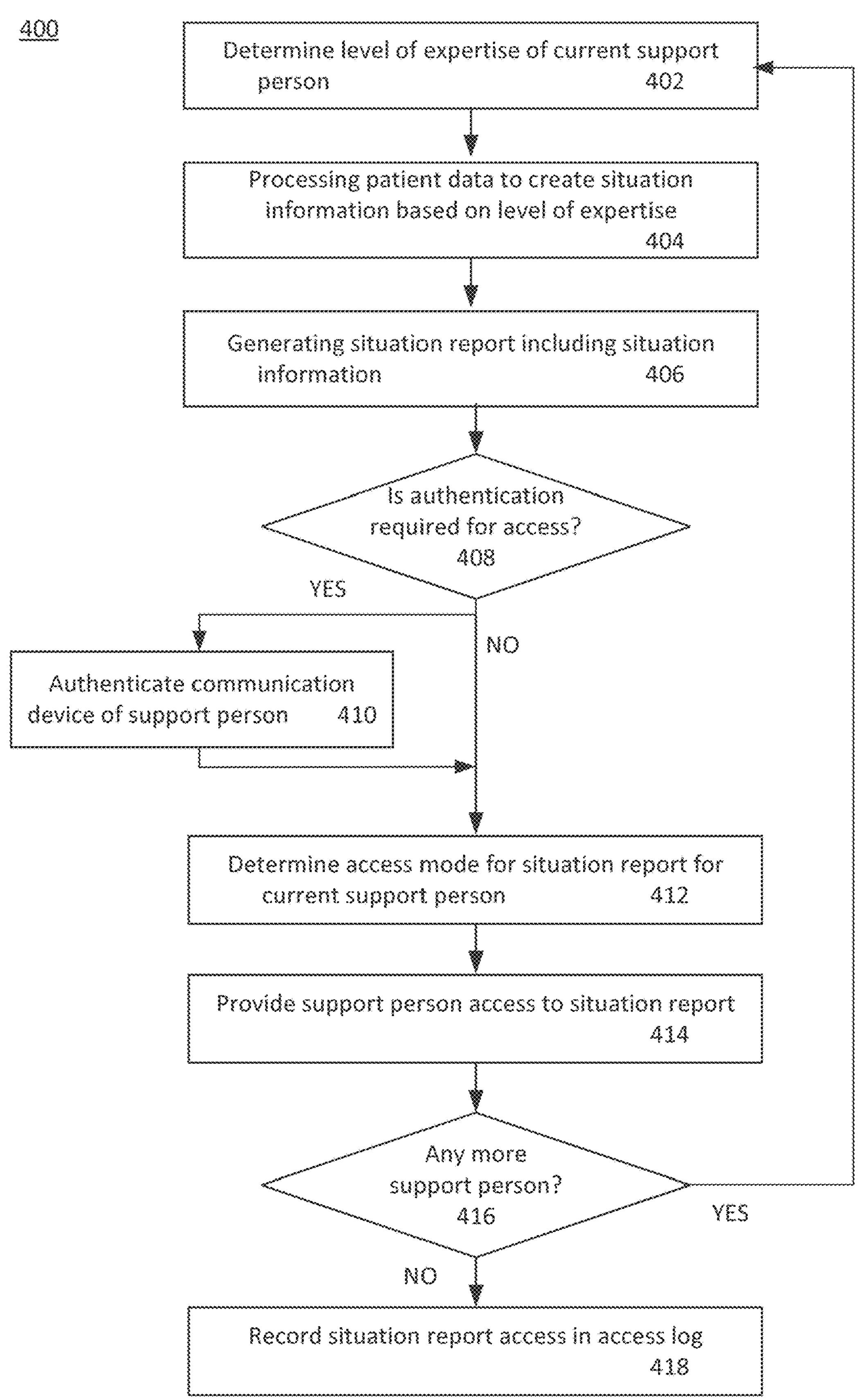
FIG. 4 is a flowchart of an example method for generating adapted situation reports tailored for various support persons, in accordance with some implementations.

FIG. 4 shows a flowchart of an example medical support process 400 for generating adapted situation reports customized to a level of expertise of support person(s) at the patient location, which is typically at a non-medical treatment site.

In block 402, a level of expertise is determined for a current support person. Various information may be received to determine the level of expertise. For example, the support person may be prompted to answer level of expertise questions, such as whether the support person is certified in CPR or other first aid procedures or training/education. In some implementations, authentication of the support person to access advanced tier situation information also serves to confirm a level of expertise. For example, a support person may be preregistered as having expertise in a particular medical area or techniques. Stored authentication data for the support person may include such level of expertise data.

Various rating systems may be employed for levels of expertise. For example, basic/intermediate/advanced levels, unexperienced/trained levels, numbering systems, such as 1-3 or 1-5 where 1 is unexperienced and 3 or 5 is a medical professional, etc. There can be two or more levels of expertise employed, such as two levels, three levels, four levels, and so on.

In block 404, patient data is processed to create situation information based on level of expertise, and optionally other adaptations. Situation reports intended for support persons with lower level of expertise may receive basic situation information applicable with basic levels of care for the patient. With higher the levels of expertise, progressively more sophisticated details may be used in the situation reports.

In some implementations, patient sensitive information, such as patient identifying information, is restricted and only presented in situation reports accessed by support persons who are preregistered, including belonging to organizations that are preregistered, as having authorization to use highly personal information. For unregistered support persons, situation information of a sensitive nature is blocked or otherwise not included in the situation report. In some cases, prior consent may be provided by the patient or patient's legal representative to permit disseminating patient sensitive information in cases of emergency.

In block 406, a situation report may be generated using the situation information processed according to block 404.

Different situation reports may be produced on the fly according to the present needs of the patient, level of expertise, availability of devices to receive the situation report, etc.

In decision block 408, it is determined whether authentication is required to access a particular tier of situation information. If authentication is required for the current support person, the process proceeds to block 410 to authenticate a communication device of the current support person. There may be a requirement of preregistration for permissible access to a particular tier of situation information. Security data may be required to be previously stored by the medical support system or stored by an external server/service that may authenticate the support person or communication device of the support person.

If authentication is not required for the current support person, the process proceeds to block 412 to optionally determine access mode for situation report for current support person. In some implementations, a standard access mode is used and the step in block 412 is skipped.

In block 414, access to the situation report is provided to the current support person. Access to the situation report is described in further detail above with regard to block 318 of FIG. 3.

In some implementations, the situation report may be interactive with the support person. For example, the support person may enter a request for specific additional situation information and the medical support system may present the requested information in an updated situation report. In some implementations, the medical support system may present prompts to the support person to request input of what particular situation information is needed by the support person.

In decision block 416, it is determined whether an additional support person is available to care for the patient in the chain of care. If an additional support person is found to be available, such the patient being moved to a different location along the chain of care or a new support person joins a current support person, the process returns to block 402 to determine a level of expertise for the new support person.

If it is determined that there are no additional support persons along the chain of care for the patient who require access to a situation report, the process proceeds to block 418 in which a record may be to log the access to the situation report(s). An access log may be used for recordation purposes. The record for the medical event may include entries for identifying information of the various support persons who accessed the situation report(s), the tier of situation information provided to each support person, time of access, care provided by the support person (if known), etc.

Figure 5:
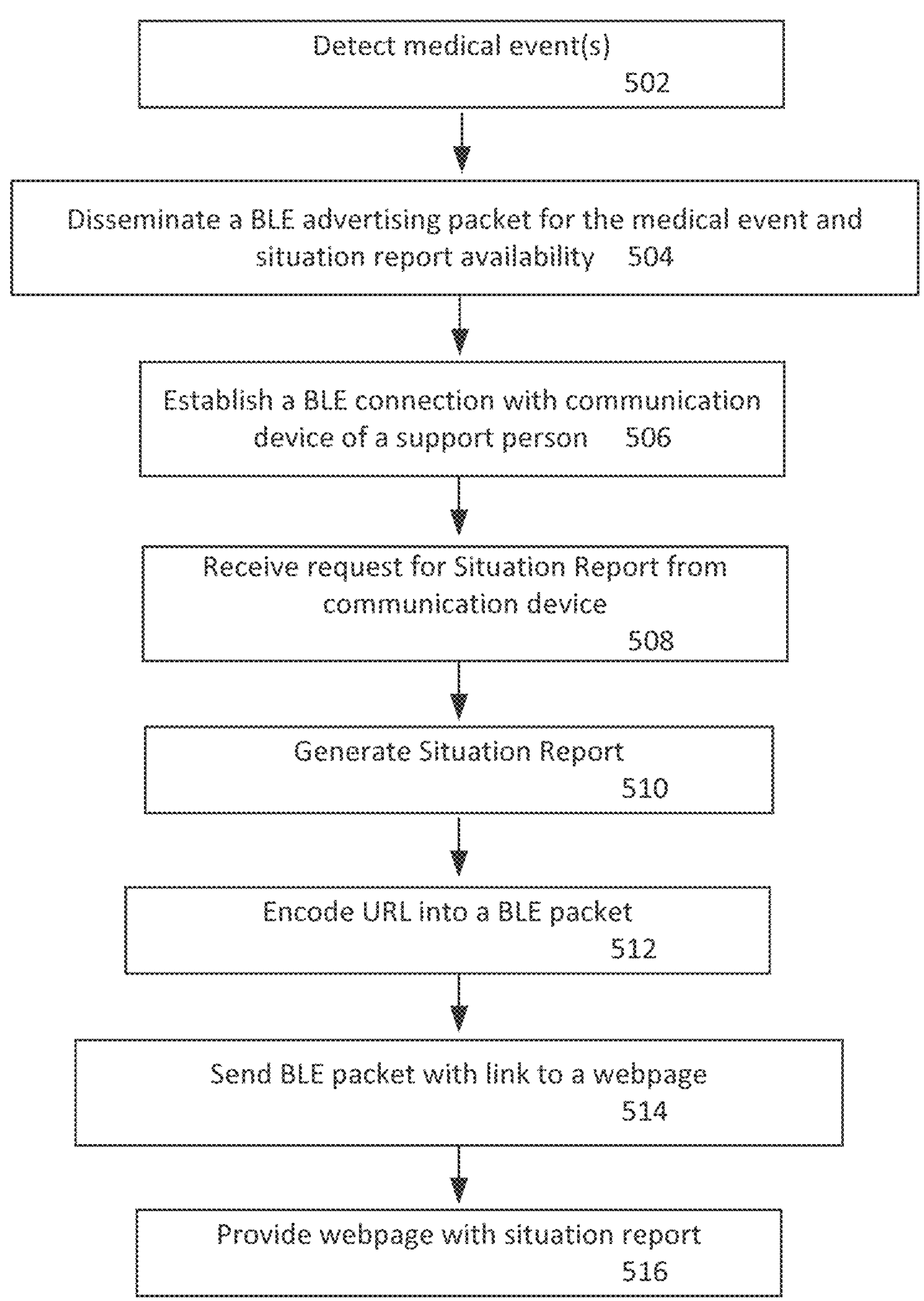
FIG. 5 is a flowchart of an example method for providing access to a situation report using BLE communication connections, in accordance with some implementations.

FIG. 5 shows a flowchart of an example medical support process 500 for enabling access to situation reports through a BLE rapid communication connection. A support person uses a communication device to connect with the wearable device of the medical support system.

In block 502, one or more medical events experienced by a patient is recognized by a wearable medical device being worn by the patient. Such detection of medical events may include the processes described in FIG. 3, step 304 above and elsewhere in this description. At times, multiple related medical events are experienced by the patient within an event time period. Such multiple medical events may be detected by the wearable medical device and each individually or collectively serve to trigger a BLE advertising packet.

As a result of detecting of the medical event(s), in block 504 the BLE advertising packet(s) is/are disseminated, such as by a beacon of the wearable medical device, for receipt by one or more communication devices of support persons within a receiving distance from the patient. The receiving distance depends on the BLE technology employed, such as 30 meters outdoors, and may be farther such as 100 meters outdoors. The receiving distance for BLE packet receipt is typically less than 50 meters, depending on any obstructions and interferences. However, advances in BLE technology may allow for farther receiving ranges to employ the medical support system.

The BLE advertising packet may include notification that a patient who is within the receiving distance is experiencing a particular medical event detected by the wearable medical device. The packet may also include a notification that a situation report is available for viewing by the support person. In some implementations, the BLE advertising packet may also include patient spotting information in the payload to assist the support person in locating the patient. The patient spotting information may include a physical description of the patient, e.g., height, hair color, race, gender, weight, etc., and/or location information that pinpoints the site of the patient. Such location information may include GPS coordinates information, a description of the objects around the patient, address, business name of the location, distance between the support person and the patient, map directions to the patient, etc.

In block 506, a BLE connection is established by the wearable device with the communication device of the support person. In some implementations, the BLE connection is made with a situation reporting application (also referred to as "application") running on the communication device (for example running in the background while other applications are being used). The situation reporting application may monitor BLE traffic and when it finds a pattern that matches a predefined BLE pattern indicating a medical event alert, the reporting application may launch a browser or screen of the reporting application on the communication device displaying a user interface to connect and accept the BLE packets from the wearable medical device.

The situation reporting application may be dedicated software for the purpose of connecting with a particular wearable medical device for detecting certain types of medical events, such as cardiovascular events, other categories of wearable medical devices, or for the purpose of connecting with a wider variety of wearable medical devices. In some implementations, the communication device may be a medical treatment device that can be employed in treating the medical event, such as an AED, and the situation reporting application resides in software of the treatment device. In some implementations, the situation reporting application may be integrated with a general health and/or fitness application that runs on a multi-purpose communication devices, such as smart phones, tablets, smart watches, etc.

The receipt of the BLE advertising packet may trigger the application to display a user interface in which the support person may interface with the medical support system. In some implementations, receipt of the BLE advertising packet may trigger a pop up notification to appear on a display of the communication device. In still some implementations, receipt of the BLE advertising packet may trigger an audio alert, vibration, or other indication on the communication device. In some implementations, receipt of the BLE advertising packet may enable the support person to interface with the medical support system through a browser of the communication device, rather than the reporting application.

In block 508, a request for the situation report may be received by the medical support system. The request may be made by the support person interacting with a user interface of the reporting application, such as activating (e.g. clicking on) an interface element on the user interface, inputting a voice command, or other forms of input.

In some implementations, the support person may opt to reject receipt of the BLE packet and refuse further information regarding the medical event of the patient. For example, the support person may activate a reject interface element on the user interface or simply ignore the notification and not interface with the medical support system within a defined period of time, such as the critical time for care. For example, when a support person does not feel qualified to address the medical event or is unavailable to provide assistance, the support person may reject further interaction with the medical support system regarding the medical event.

Furthermore, should the support person move outside of the receiving range for BLE transmissions, the support person may not receive further BLE packets and in some cases will cease to interact with the medical support system for the current medical event unless the support person connected with the remote computing device of the support system prior to traveling away from the patient.

In some implementations, the situation report application may enable the support person to forward the notification/alert of a nearby medical event to another support person to assist the patient. Once the alternative support person is within receiving range of the wearable device, the BLE communication connection may additionally be made with the communication device of this additional support person, as described above.

In block 510, the situation report may be generated as described above, for example as describe with regards to FIG. 3. In block 512, a BLE packet may be encoded with a UUID in the payload for a service to provide a situation report for a medical event. The BLE communication that has link information encoded on a characteristic, e.g., a URL and/or a persistent unique identifier (PUID) for the medical device. The link information enables access to the remote computing device, such as 210 in FIG. 2, including situation reports generated and/or stored by the remote computing device and accessible via one or more webpages. The BLE packet that includes the link may be a BLE advertising packet, such as the initial BLE advertising packet that establishes connection, or a separate BLE advertising packet or sub-packet. In some implementations, the BLE packet may be a scan response packet provided subsequent to disseminating the initial BLE advertising packet and after the communication connection is established.

In some implementations, the BLE packet may be encoded with a UUID for standard care instructions for the particular detected medical event. In such implementations, the standard care instructions may be provided as preliminary information for initiating care in the BLE packet or otherwise transmitted, displayed, or outputted to the support person. The situation report may provide more comprehensive and patient-specific care information than such standard instructions. Examples of such preliminary care information may include, for ventricular fibrillation, standard instructions to find an AED. A finding of an asystole event may be associated with standard instructions to perform CPR. A detected fall experienced by a patient may result in standard instructions to look for wounds or assess for a seizure. However, the situation report may provide more comprehensive situation information, such as a fall that resulted from another detected medical event may be associated with instructions to treat the initiating medical event first.

The BLE packet encoded with the link is sent from the wearable medical device, in block 514. As described above, the BLE packet may be the BLE advertising packet configured with the link data in the payload. In other implementations, the BLE packet may be a scan response packet transmitted at the same time or after the BLE advertising packet is transmitted.

In block 516, the one or more webpages that display the situation report is provided to the communication device upon activation of the link (e.g., clicking on a hyperlink) by the support person. Such access to the situation report is described above with regards to FIG. 3 and FIG. 4.

In some implementations, the communication connection may be bi-directional and the communication device can initiate requests for information to the medical support system. For example, the support person can send to the wearable device, a BLE packet encoded with a request for particular information in a situation report, such as an ECG. Other ways of transmitting a request from the communication device to the wearable medical device and/or remote computing device are possible.

In response to the request for additional information, access may be provided to the requested information. For example, the situation report may be dynamically viewed and updated as needed on the fly to enable viewing of some (additional) situation information and/or to restrict viewing of certain situation information. In some implementations, in response to the request another link may be sent to the communication device to access the additional information, which may be presented on another webpage or information source. In some cases, such as when high tier details, such as patient sensitive information is requested by the support person, the support person may need to be checked as being pre-authorized prior to providing the requested information, e.g., updating the webpage. For example, the medical support system may confirm that the situation reporting application on the communication device indicates pre-authorization of the support person.

Other communication connections between the wearable medical device and a communication device of the support person are possible. For example, the wearable medical device may include an infrared port to transmit infrared signals to the communication device, similar to a BLE packet described above. The communication device may be enabled for infrared communications with an infrared receiver and/or transmitter, e.g., according to Infrared Data Association (irDA) specifications, such as a smartphone or specialized medical treatment device, e.g., AED. The irDA port of the communication device may be held to the wearable device in a position free of objects blocking the communication path. The wearable device may provide written instructions, such as on a display or text on a label, for the support person on steps to connect via infrared communication, such as activating the irDA port of the communication device.

In still some implementations, the communication connection may be made with use of audio data transmission, such as an acoustic (e.g., audible) QR code. An audio pattern may be transmitted from a speaker on the wearable medical device in which link data is encoded. The communication device may receive audio signals via a receiver. The reporting application may be configured to translate the audio patterns into the link, which may be displayed on the communication device for activation by the support person.

Some or all of the medical support processes 300 in FIG. 3, 400 in FIG. 4, and 500 in FIG. 5, or any other processes described herein, or variations and/or combinations of those processes, may be performed under the control of one or more computer systems configured with executable instructions and/or other data, and may be implemented as executable instructions executing collectively on one or more processors. For example, the medical support process 300, 400 and/or 500 may be adapted to include steps for treating a patient, such as a defibrillator shock based on the determined episodes.

Figure 6:
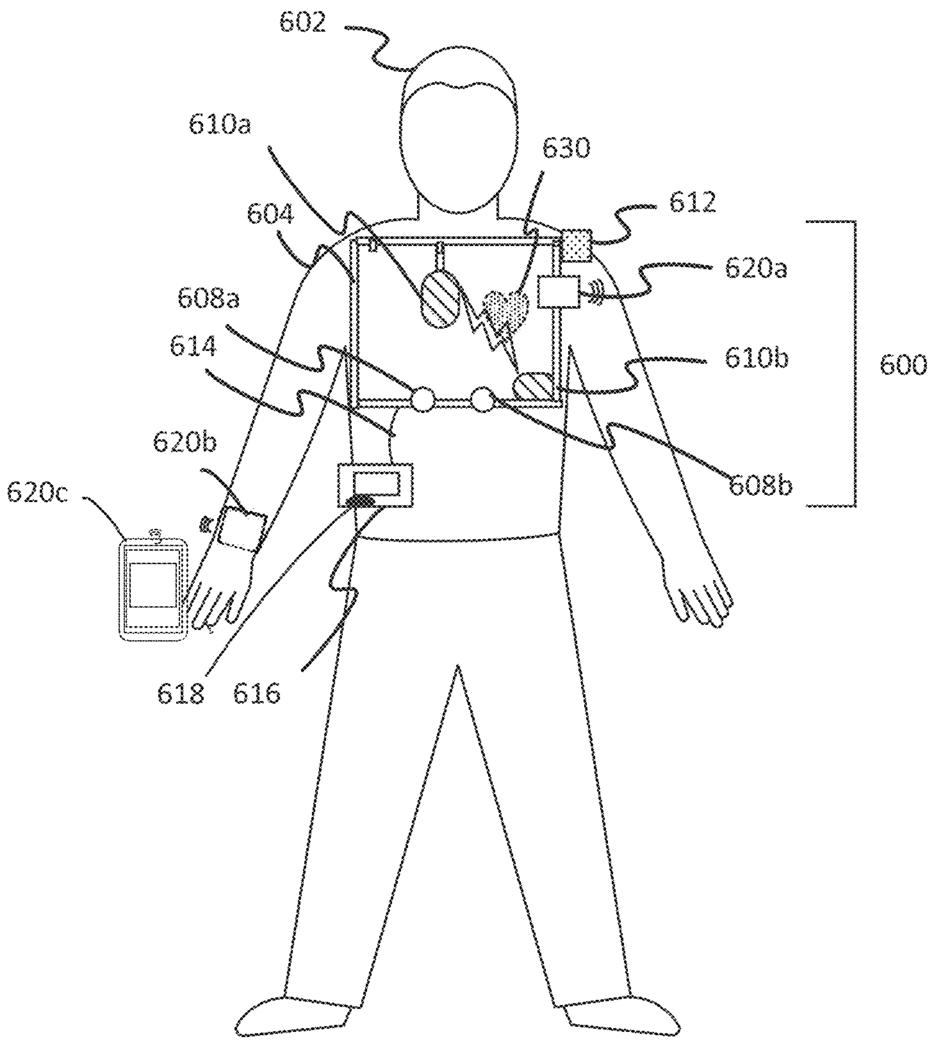
FIG. 6 is a schematic diagram of a wearable medical device including a vest-type wearable article with components for use in the medical support system, in accordance with some implementations.

FIG. 6 shows an example of a wearable medical device in the form of a wearable cardioverter defibrillator (WCD) 600 configured with components for cardiac monitoring and treatment. The WCD 600 includes a vest-type wearable article 604 that houses various components such as electrode sensors, one or more sensor 612, and an electronic main unit 616 in communication with the components of the wearable article 604. In some implementations, the main unit 616 may be carried by the patient separately from the wearable article 604, such as with a purse, belt, strap over the shoulder, and so on.

The main unit may include an interface port 618 to perform various rapid communication connections, such as presenting a scannable QR code, broadcasting a BLE advertising packet including the link, sending RFID signals with the link embedded, transmitting the link with NFC, sending Zigbee signals, and emitting a pattern of audio signals corresponding to the link.

In some implementations, the wearable article 604 is configured for continuous wear (e.g., for at least several hours per day, and for at least several days, even a few months) by a patient 602, as may be prescribed by a medical provider. The wearable article 604 (also referred to as a "support structure") may be worn under clothing and has multiple electrocardiogram (ECG) electrodes 608*a*, 608*b* that contact the skin of the patient at particular locations on the patient torso in order to monitor the cardiovascular condition of the patient when in use. Defibrillation electrodes 610*a*, 610*b* also be positioned when in use to contact the skin of the patient at torso locations to discharge electrical charge. More than two ECG electrodes can be used and distributed around a patient's body.

Some aspects of the WCD 600 include a housing and an energy storage module (not shown) within the housing. The energy storage module can be housed within the defibrillator and can be configured to store an electrical charge. Other components can cause at least some of the stored electrical charge to be discharged via electrodes 610*a*, 610*b* through the patient, so as to deliver one or more defibrillation shocks through the patient. A lubricant may also be ejected from one or more ports (not shown) in the wearable device 600 near or at the electrodes for conductive contact.

The main electronic unit 616 may encase various software components of the wearable device 600. For example, the main unit 616 may include the data collection module 204 and/or access module 206 with reference to FIG. 2, and/or various subcomponents. The main electronic module 616 may initiate defibrillating treatment using defibrillation electrodes 610*a*, 610*b*, or hold-off defibrillation, based on a variety of inputs, and/or signal outputs, including the ECG signal obtained using ECG electrodes 608*a*, 608*b*.

The plurality of electrodes 608*a*, 608*b*, 610*a*, 610*b*, can be coupled to a processor and/or main unit 616 via one or more cables 614, such as a therapy cable and/or ECG leads. ECG electrodes 608*a*, 608*b* and/or defibrillation electrodes 610*a*, 610*b* can be configured to be worn by a patient 602 in a number of ways. For instance, electrodes 608*a*, 608*b*, 610*a*, 610*b* can be coupled to the wearable article 606, directly or indirectly. The wearable article 606 can be configured to be worn by patient 602 so as to maintain electrodes on the body of the patient, often while the patient is moving around, etc. The electrodes can be thus maintained on the body by being attached to the skin of patient, or by being pressed against the skin directly or through garments, etc. In some embodiments the electrode is not necessarily pressed against the skin, but becomes biased that way upon sensing a condition that could merit intervention by the WCD system.

Using electrodes 608*a*, 608*b* the WCD can detect a shockable rhythm and administer a brief, strong electric pulse (e.g., shock, defibrillation shock, therapy, electrotherapy, therapy shock) through the body of the patient through defibrillation electrodes 610*a*, 610*b* in attempts to bring back a normal heart rhythm. The electric pulse is intended to go through and restart the heart 630, in an effort to save the life of patient 602. In some instances, the electric pulse can include one or more pacing pulses of lesser magnitude to simply pace the heart 630 if needed.

The wearable article 604 can be implemented in many different ways. For example, it can be implemented in a single component or a combination of multiple components. In embodiments, the wearable article 604 could include a vest, a half-vest, a garment, etc. In such embodiments such items can be worn similarly to analogous articles of clothing. In embodiments, the wearable article 604 could include a harness, one or more belts or straps, etc. In such embodiments, such items can be worn by the patient around the torso, hips, over the shoulder, etc. In embodiments, wearable article 604 can include a container or housing, which can even be waterproof. In such embodiments, the support structure can be worn by being attached to the patient's body by adhesive material, for example as shown and described in U.S. Pat. No. 8,024,037. The wearable article 606 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples as well. It will be understood that the wearable article 606 is shown only generically in FIG. 6, and in fact partly conceptually. FIG. 6 is provided merely to illustrate concepts about wearable article 604 and is not to be construed as limiting how the wearable article 604 is implemented, or how it is worn.

The wearable device 600, according to some implementations, can obtain various additional data from patient 602. To gather such patient data, the medical device may optionally include one or more sensor(s) 612 (including electrodes 608*a*, 608*b*, 610*a*, 610*b*). In some implementations, the sensor 612 could be provided as a standalone device, for example separate from the wearable article 604 or housing of the WCD 600. Sensor 612 may include one or more sensor in an array or a plurality of independent sensors, may be physically coupled to, in communication with, or integrated with the wearable article 604 or other medical device components. Such communication can be implemented by a communication module, as will be deemed applicable by a person skilled in the art in view of this description.

Sensor 612 can be configured to sense or monitor at least one local parameter, such as a parameter of patient 602, a parameter of the WCD system, and/or a parameter of the environment. The sensor renders a signal responsive to the sensed parameter. The signal may be interpreted as quantitative data, such as values of a sensed parameter, or qualitative data, such as a comparison of the data to a threshold value. In some implementations, the signal is in the form of a qualitative, such as informing whether or not a threshold is met, and so on. Sometimes these inputs about patient 602 are also referred to herein as physiological inputs and patient inputs. In embodiments, a sensor can be construed more broadly, as encompassing many individual sensors.

The sensors may include the electrodes described above. Other examples of sensors may include a perfusion sensor, a pulse oximeter, a device for detecting blood flow (e.g. a Doppler device), a sensor for detecting blood pressure (e.g. a cuff), an optical sensor, illumination detectors and sensors working together with light sources for detecting color change in tissue, a device that can detect heart wall movement, a sound sensor, a device with a microphone, a Saturation of Peripheral Oxygen (SpO2) sensor, a GPS, patient temperature thermometer, pressure sensors, optical sensors such as photoplethysmography, etc. to produce signals used in generating health data about the patient. An audio detector, e.g., microphone, such as heart-sound/phonocardiogram may be positioned to detect frequency, volume, intensity, regularity, etc. of internal body functions, such as heart beat. The microphone may also detect frequency, volume, regularity, etc. of breaths.

Various patient communication devices may be employed for support persons to interact with the medical support system, such as communicate with the remote computing device. Interactions may include output the situation report, input a level of expertise of a support person, output instruction information, input authentication information, scan a bar code to access the situation report, etc. Various types of patient communication devices may include an interface port, shown by example as 618 on main unit 616. Examples of patient communication devices may include an a microphone/speaker component 620*a* of the wearable article 604, a smartwatch 620*b* of the patient, a mobile phone 620*c* (e.g., patient communication device 216 in FIG. 2), and the main unit 616. In some implementations the a microphone/speaker component 620*a* may output a pattern of audio signals corresponding to a link to the situation report, for a rapid communication connection. Other patient communication devices are possible that employ various input and/or output modalities. The patient communication device may also be located on a wearable article component of the medical device and can include a touch screen, a speaker, etc.

The wearable article 604 shown in FIG. 6 illustrate a vest-type garment wearable medical monitoring device. In some implementations, the medical monitoring device may take various forms or combination of forms. For example, the wearable structure may include one or more patches, one or more bands, and/or a torso fitted garment to house various components of the medical monitoring device.

Figure 7:
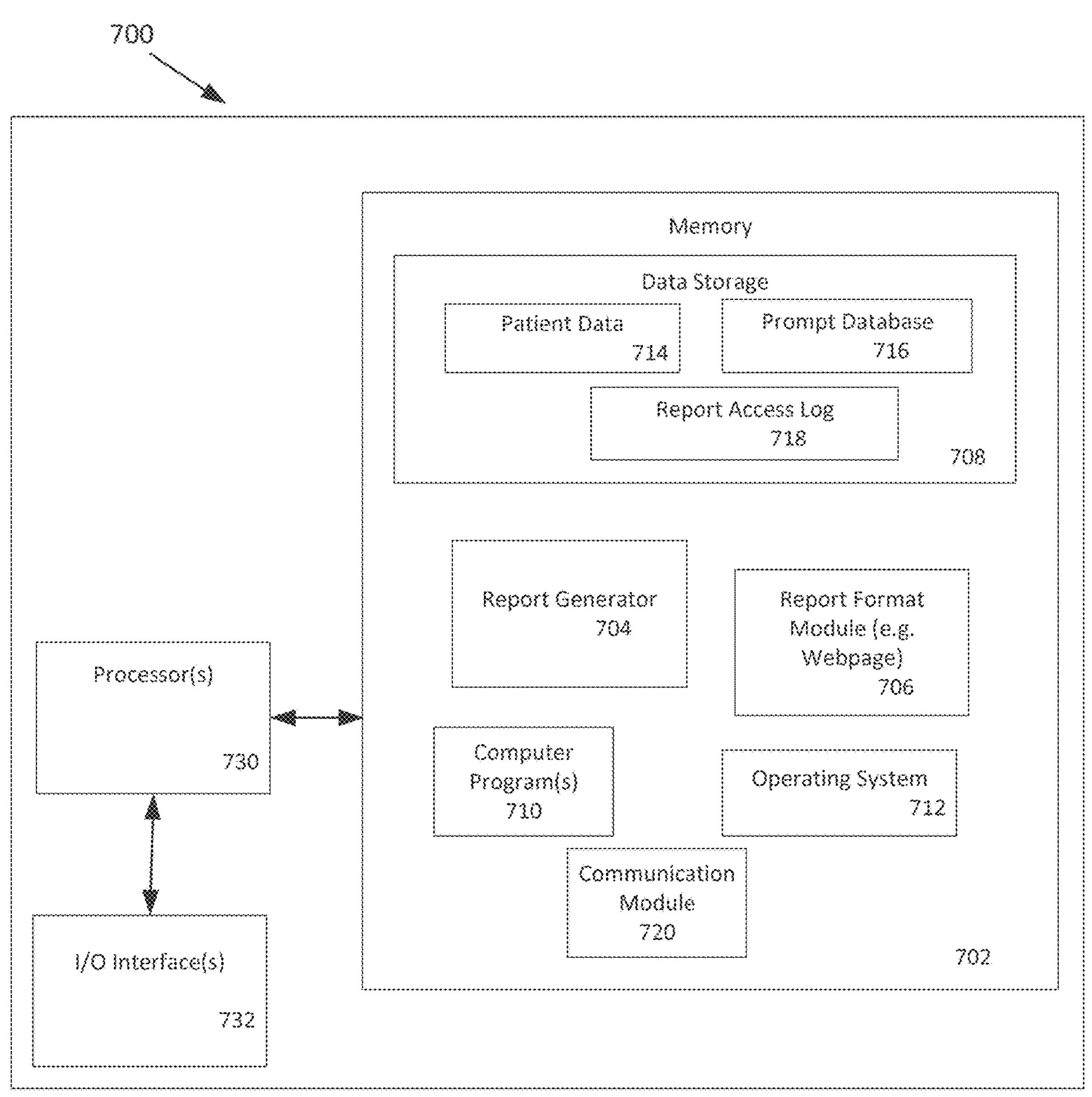
FIG. 7 is a block diagram illustrating an example of the remote computing device upon which at least some of the medical support processes may be implemented, in accordance with some implementations.

FIG. 7 shows an example remote computing device 700, such as 210 in FIG. 2, which may implement some of the medical support processes described herein. The remote computer device 700 may include memory 702, processor 730, and I/O interface 732. The various elements of the remote computing device 700 are shown in FIG. 7 as discrete/separate elements for purposes of illustration and explanation. According to some implementations, it is possible to combine some of these elements into a single element or device, while in other implementations of the medical support system, these elements may be distributed across a network such as in a cloud computing network. For example, functions of the medical support system may be performed by one or both of the multiple remote computing device in a distributed network to provide information to other various devices of the support system and/or personal communication devices (such as the support person communication device) and perform other tasks as a service. Some of the components and functions depicted in remote computing device 700 may be provided by the wearable medical device (item 202 in FIG. 2) in addition to or instead of remote computing device 700.

The processor 730 processes instruction for execution within the remote computing device 700 including instructions stored in memory 702 or on the data store 708. The processor 730 may coordinate computing device components, e.g. applications, wireless or wired communication through interfaces, etc. In some implementations, multiple processors and buses may be used.

In some implementations, processor 730 may include intelligent hardware, e.g., a central processing unit (CPU), a microcontroller, an application specific integrated circuit (ASIC), etc. The processor 730 may be implemented in a number of ways. Such ways include, by way of example and not limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 730 may be implemented as a chipset of chips that include separate and multiple analog digital processors. The processor may also be implemented using various architectures. For example, the processor 730 may be a CISC (Complex Instruction Set Computer) processor, RISC (Reduced Instruction Set Computer) processor or MISC (Minimal Instruction Set Computer) processor, mobile device processors, etc.

The "processor" as used herein, includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

Processor 730 may include, or have access to, a non-transitory storage medium, such as a memory 702, which can work together with processor 730. The memory 702 is for storing information within the remote computing device 700. Memory 702 may include various dynamic storage devices, coupled to a bus for storing information and instructions to be executed by the processor 730. The memory 702 may also be used for storing temporary variables or other intermediate information during execution of instructions to be executed by the processor 730. Such instructions, when stored in non-transitory storage media accessible to the processor 730, render the remote computer system 700 into a special-purpose machine that is customized to perform the operations specified in the instructions.

Memory 702 can include programs for processor 730, which processor 730 may be able to read and execute. More particularly, the programs can include sets of instructions in the form of code, which processor 730 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 730, and can also include protocols and ways that decisions can be made.

The memory 702 may be any suitable data storage, memory and/or non-transitory computer-readable storage media, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor 730. For example, a tangible medium such as a hardware storage device can be used to store the control logic, which can include executable instructions. The instructions can also be contained in, and provided as, an electronic signal.

Data store 708 may store various data including patient data 714 that may be received from the wearable device or other data input sources and/or generated by the remote computing device 700.

Data store 708 may further include a prompt database 716 that stores prompts (such as standard instructions to care for a medical event) to be used for a support person for a particular medical event. For example, the prompt database 716 may include one or more tables organizing various prompts, such as instructions on care, instructions on how to access the situation report, request for input of support person information such as a level of expertise, warnings, basic background information about the wearable device and/or medical event, etc. The tables may associate such prompts with different medical events. When a medical event is identified, the prompts may be included in the situation report or presented automatically prior to receiving the situation report.

Data store 708 may further include a report access log 718 that stores descriptions of times that a situation report was previously or currently accessed such as previous and current situation reports (such as a reference to the stored situation report), medical event associated with the situation report, time of access, level of expertise of the support person, identification and/or contact information for the support person, location of support person when accessing the situation report, mode of communicating the situation report, etc.

In some implementations, at least a portion of information may be stored on a disk drive or other computer readable storage device (not shown) within the remote computing device 700. Such storage device include a floppy disk device, a hard disk device, an optical disk device, or a tape device, digital cards, a flash memory or other similar solid state memory device, or an array of devices.

Memory 702 further includes the situation report generator 704, such as situation report generator 212 described above with regards to FIG. 2. A report formatting module 706 of the memory 702 may be a webpage module 214 as described above with regards to FIG. 2. Other report formats are possible, such as audio situation reports.

Various modules or other computer programs 710, also referred to as programs, software, software applications or code, are stored within memory 702 and contain instructions that, when executed, perform one or more methods, such as those described herein. In some implementations, and as a matter of convention used herein, instances of the software may be referred to as a "module" and by other similar terms. Generally, a module includes a set of the instructions so as to offer or fulfill a particular functionality. Implementations of modules and the functionality delivered are not limited by the implementations described in this document. The computer program may be tangibly embodied in an information carrier such as computer or machine readable medium, for example, the memory 802, storage device or memory on processor 730. A machine readable medium is any computer program product, apparatus or device used to provide machine instructions or data to a programmable processor.

Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time.

A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The remote computing device 700 may implement the techniques described herein using customized hard-wired logic, one or more ASICs or FPGAs, firmware and/or program logic which in combination with the computer system causes or programs the remote computing device 700 to be a special-purpose machine. According to one implementation, the techniques herein are performed by the remote computing device 700 in response to the processor 730 executing one or more sequences of one or more instructions contained in the memory 702. Such instructions may be read into the memory 702 from another storage medium. Execution of the sequences of instructions contained in the memory 702 causes the processor 730 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 712.

Remote computing device 700 further includes the operating system 712. Any operating system 712, e.g., server OS, that is supports the medical support processes described herein performed by the remote computing device 700 may be employed.

The communication module 720 may also include software that enables communications of the user interface 730 over a network such as the HTTPS, TCP/IP, RTP/RTSP, protocols, wireless application protocol (WAP), IEEE 802.11 protocols, and the like. In addition to and/or alternatively, other communications software and transfer protocols may also be used, for example IPX, UDP or the like. The communication network may include a local area network, a wide area network, a wireless network, an Intranet, the Internet, a private network, a public network, a switched network, or any other suitable communication network, such as for example cloud networks. The network may include many interconnected computer systems and any suitable communication links such as hardwire links, optical links, satellite or other wireless communications links such as Bluetooth, Wi-Fi, wave propagation links, or any other suitable mechanisms for communication of information. For example, the network may communicate to one or more mobile wireless devices, such as mobile phones, tablets, and the like, via a base station such as a wireless transceiver.

The Input/Output (I/O) interface 730 can interface to other input and output devices. In some implementations, the I/O interface 730 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. Flowcharts as in FIGS. 3 and 4 are used to describe both programs and also methods. So, while flowcharts described methods in terms of blocks, they also concurrently describe programs. It is also within the spirit and scope to implement a program or code that can be stored in a machine-readable medium, such as logic including software instructions encoded in one or more non-transitory media for execution by the one or more processors, to permit a computer to perform any of the methods described above.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A method for a cardioverter defibrillator support system to create a situation report for access in assisting a patient, the method comprising:

gathering patient data by a wearable medical device of a patient wearing the wearable medical device;

based, at least in part on the patient data, determining by the wearable medical device that the patient experiences a medical event including one or more arrythmias when the patient is away from a medical treatment site;

initiating defibrillation treatment for the medical event by the wearable medical device;

determining a level of expertise of a support person as a bystander or a rescuer at a location of the patient during a critical time for care;

extracting from the patient data, expertise-appropriate situation information based, at least in part, on the determined level of expertise;

generating from the extracted patient data, by at least one of a remote computing device and/or the wearable medical device, the situation report including the extracted patient data related to one or more occurrences associated with the medical event that satisfy one or more situation factors; and providing, by at least one of a remote computing device and/or the wearable medical device, to the support person at the location of the patient during the critical time for care, access to the situation report for use by the support person in caring for the patient.

2. The method of claim 1, wherein generating the situation report includes determining an event time period related to the medical event and/or the patient and the one or more situation factors include occurrences corresponding to the event time period.

3. The method of claim 1, wherein the situation report includes situation information related to at least one characteristic of the one or more arrhythmias and/or at least one characteristic of the defibrillation treatment.

4. The method of claim 1, wherein providing access to the situation report comprises:

generating a webpage that includes the situation report specific for a tier of detail consistent with the level of expertise; and delivering linking data to the webpage via a rapid communication connection to a communication device of the support person, by at least one of: presenting a scannable quick response (QR) code, broadcasting a Bluetooth low energy (BLE) advertising packet including the linking data, sending radio frequency identification (RFID) signals with the linking data embedded, transmitting the linking data with near-field communication (NFC), or emitting a pattern of audio signals corresponding to the linking data.

5. The method of claim 4, wherein delivering the linking data includes transmitting the BLE advertising packet having a universally unique identification (UUID) for a service that includes situation reporting for the medical event.

6. The method of claim 4, wherein providing access includes:

authenticating the support person to access a particular tier of detail provided in the situation report; and presenting a prompt to the support person to pair the cardioverter defibrillator support system with the communication device of the support person.

7. A method for a medical support system to provide access to a situation report in assisting a patient, the method comprising:

determining, by a wearable medical device of a patient, that at least one medical event is experienced by the patient away from a medical treatment site;

determining a level of expertise of a support person as a bystander or a rescuer at a location of the patient during a critical time for care;

extracting from the patient data, expertise-appropriate situation information based, at least in part, on the determined level of expertise;

in response to determining the at least one medical event, establishing a Bluetooth low energy (BLE) connection with a communication device of the support person, wherein establishing the connection includes:

disseminating a BLE advertising packet to advertise the at least one medical event and availability of the situation report that includes extracted patient data related to one or more occurrences associated with the at least one medical event, wherein the BLE advertising packet is configured to be received by an application running on the communication device;

receiving a response from the communication device requesting access to the situation report;

delivering by the wearable medical device via a BLE packet, linking data to a remote computing device for accessing the situation report; and providing access to the situation report by using the linking data.

8. The method of claim 7, wherein the BLE advertising packet includes a universally unique identification (UUID) for a service of providing the situation report.

9. The method of claim 7, wherein the BLE advertising packet includes patient spotting information including at least one of: patient location information or a physical description of the patient to assist in locating the patient.

10. The method of claim 7, wherein the BLE connection is bidirectional and the method further comprises:

receiving from the communication device, a request for particular additional situation information in the situation report; and providing access to the additional situation information.

11. The method of claim 10, further comprising:

prior to providing access to the additional situation information, determining that the support person is approved for high tier details in the situation report by confirming that the application on the communication device indicates pre-authorization of the support person.

12. The method of claim 7, wherein the linking data enables access to a webpage that includes the situation report specific for a tier of detail consistent with the level of expertise.

13. The method of claim 7, wherein the at least one medical event includes multiple related medical events occurring within an event time period.

14. A medical support system for to create information reports for access in assisting a patient, the medical support system comprising:

a wearable medical device of the patient wearing the wearable medical device and configured to gather patient data, the wearable medical device comprising:

a patient assessment module to determine that the patient experiences a medical event, based at least in part on the patient data;

one or more treatment components to deliver treatment for the medical event to the patient; and at least one remote computing device comprising:

an interface to communicate with the wearable medical device; and disposed in the wearable medical device and/or the at least one remote computing device, one or more processors and logic encoded in one or more non-transitory media for execution by the one or more processors and when executed operable to perform steps comprising:

determining a level of expertise of a support person as a bystander or a rescuer at a location of the patient during a critical time for care;

extracting from the patient data, expertise-appropriate situation information based, at least in part, on the determined level of expertise;

generating by a data generator module, a situation report including the extracted patient data related to one or more occurrences associated with the medical event; and providing by an access module, access for the support person at the patient location, to the situation report for use in caring for the patient during the critical time for care of the patient.

15. The medical support system of claim 14, wherein the logic of the one or more processors is further operable to perform steps comprising:

determining instruction information based, at least in part, on the situation report; and providing, by the access module, access for the support person to the instruction information during the critical time for care.

16. The medical support system of claim 14, wherein the situation report includes patient context information.

17. The medical support system of claim 14, wherein the remote computing device further comprises:

a webpage module for generating a webpage including the situation report specific for a tier of detail consistent with the level of expertise and accessible via linking data provided by a rapid communication connection by an interface port of the wearable medical device configured to perform at least one of:

presenting a scannable quick response (QR) code, broadcasting a Bluetooth low energy (BLE) advertising packet including the linking data to the webpage, sending radio frequency identification (RFID) signals with the linking data embedded, transmitting the linking data with near-field communication (NFC), or emitting a pattern of audio signals corresponding to the linking data.

18. The medical support system of claim 14, wherein providing access includes steps comprising:

authenticating the support person to access a particular tier of detail provided in the situation report; and presenting a prompt to the support person to pair the medical support system with a communication device of the support person.

19. The method of claim 1, wherein when the level of expertise of the support person is determined as a bystander, extracting from the patient data includes removing patient identifying information.

20. The medical support system of claim 14, wherein when the level of expertise of the support person is determined as a bystander extracting from the patient data includes removing patient identifying information.

* * * * *